US011520415B2

(12) United States Patent
Douglas et al.

(10) Patent No.: US 11,520,415 B2
(45) Date of Patent: Dec. 6, 2022

(54) INTERACTIVE 3D CURSOR FOR USE IN MEDICAL IMAGING

(71) Applicant: D3D Technologies, Inc., Orlando, FL (US)

(72) Inventors: Kathleen M. Douglas, Winter Park, FL (US); Robert E. Douglas, Winter Park, FL (US); David Byron Douglas, Winter Park, FL (US)

(73) Assignee: D3D Technologies, Inc., Orlando, FL (US)

( * ) Notice: Subject to any disclaimer, the term of this patent is extended or adjusted under 35 U.S.C. 154(b) by 0 days.

(21) Appl. No.: 17/339,341

(22) Filed: Jun. 4, 2021

(65) Prior Publication Data

US 2021/0294435 A1    Sep. 23, 2021

Related U.S. Application Data

(63) Continuation of application No. 17/122,518, filed on Dec. 15, 2020, now Pat. No. 11,036,311, which is a (Continued)

(51) Int. Cl.
*G06F 3/0346* (2013.01)
*G06F 3/04812* (2022.01)
(Continued)

(52) U.S. Cl.
CPC .......... *G06F 3/0346* (2013.01); *A61B 5/489* (2013.01); *A61B 6/466* (2013.01); (Continued)

(58) Field of Classification Search
CPC ..... H04N 13/344; A61B 6/466; G06F 3/0346; G06F 3/03543; G06F 3/04812; G06F 3/04815; G06F 3/04842
See application file for complete search history.

(56) References Cited

U.S. PATENT DOCUMENTS 4,472,737 A    9/1984  Iwasaki
4,808,979 A    2/1989  DeHoff et al.
(Continued)

FOREIGN PATENT DOCUMENTS

CN       1885233 A    12/2006
CN     102968791 A     3/2013
(Continued)

OTHER PUBLICATIONS

U.S. Appl. No. 60/673,257, filed Apr. 20, 2005, Bar-Zohar et al.
(Continued)

*Primary Examiner* — Robin J Mishler
(74) *Attorney, Agent, or Firm* — Amsel IP Law PLLC; Jason Amsel

(57) ABSTRACT

An interactive 3D cursor facilitates selection and manipulation of a three-dimensional volume from a three-dimensional image. The selected volume image may be transparency-adjusted and filtered to remove selected tissues from view. Qualitative and quantitative analysis of tissues in a selected volume may be performed. Location indicators, annotations, and registration markers may be overlaid on selected volume images.

23 Claims, 16 Drawing Sheets

Related U.S. Application Data continuation of application No. 17/021,548, filed on Sep. 15, 2020, now Pat. No. 10,936,090, which is a continuation of application No. 15/878,463, filed on Jan. 24, 2018, now Pat. No. 10,795,457, which is a continuation-in-part of application No. 14/877,442, filed on Oct. 7, 2015, now Pat. No. 9,980,691, which is a continuation-in-part of application No. 12/176,569, filed on Jul. 21, 2008, now Pat. No. 9,349,183, which is a continuation-in-part of application No. 11/941,578, filed on Nov. 16, 2007, now Pat. No. 8,384,771.

(60) Provisional application No. 60/877,931, filed on Dec. 28, 2006.

(51) Int. Cl.
   G06F 3/04842 (2022.01)
   G06F 3/0354 (2013.01)
   G06T 19/00 (2011.01)
   A61B 6/00 (2006.01)
   G06T 7/62 (2017.01)
   G06T 7/00 (2017.01)
   H04N 13/344 (2018.01)
   H04N 13/183 (2018.01)
   A61B 5/00 (2006.01)

(52) U.S. Cl.
   CPC ...... G06F 3/03543 (2013.01); G06F 3/04812 (2013.01); G06F 3/04842 (2013.01); G06T 7/0012 (2013.01); G06T 7/0014 (2013.01); G06T 7/62 (2017.01); G06T 19/00 (2013.01); G06T 19/006 (2013.01); H04N 13/183 (2018.05); H04N 13/344 (2018.05); G06T 2207/10072 (2013.01); G06T 2207/10081 (2013.01); G06T 2207/10104 (2013.01); G06T 2207/20104 (2013.01); G06T 2207/30096 (2013.01); G06T 2207/30204 (2013.01); G06T 2210/41 (2013.01)

(56) References Cited

U.S. PATENT DOCUMENTS

| | | |
|---|---|---|
| 4,870,600 A | 9/1989 | Hiraoka |
| 4,871,233 A | 10/1989 | Sheiman |
| 4,952,024 A | 4/1990 | Gale |
| 4,896,210 A | 6/1990 | Brokenshire et al. |
| 4,987,527 A | 1/1991 | Hamada et al. |
| 5,049,987 A | 9/1991 | Hoppenstein |
| 5,113,285 A | 5/1992 | Franklin et al. |
| 5,146,687 A | 9/1992 | Kjellstrom |
| 5,162,897 A | 11/1992 | Jitsukata et al. |
| 5,200,819 A | 4/1993 | Nudelman et al. |
| 5,233,458 A | 8/1993 | Moffitt et al. |
| 5,278,884 A | 1/1994 | Eberhard et al. |
| 5,287,437 A | 2/1994 | Deering |
| 5,293,529 A | 3/1994 | Yoshimura et al. |
| 5,345,281 A | 9/1994 | Taboada et al. |
| 5,371,778 A | 12/1994 | Yanof et al. |
| 5,402,191 A | 5/1995 | Dean et al. |
| 5,488,952 A | 2/1996 | Schoolman |
| 5,493,595 A | 2/1996 | Schoolman |
| 5,510,832 A | 4/1996 | Garcia |
| 5,524,187 A | 6/1996 | Felner et al. |
| 5,541,641 A | 7/1996 | Shimada |
| 5,564,810 A | 10/1996 | Larson |
| 5,566,280 A | 10/1996 | Fukui et al. |
| 5,621,867 A | 4/1997 | Murata et al. |
| 5,627,582 A | 5/1997 | Muramoto et al. |
| 5,644,324 A | 7/1997 | Maguire, Jr. |
| 5,659,625 A | 8/1997 | Marquardt |
| 5,682,172 A | 10/1997 | Travers et al. |
| 5,682,437 A | 10/1997 | Okino et al. |
| 5,696,521 A | 12/1997 | Robinson et al. |
| 5,708,359 A | 1/1998 | Gregory et al. |
| 5,714,997 A | 2/1998 | Anderson |
| 5,734,416 A | 3/1998 | Ito et al. |
| 5,745,163 A | 4/1998 | Nakamura et al. |
| 5,822,117 A | 10/1998 | Kleinberger et al. |
| 5,841,830 A | 11/1998 | Barni et al. |
| 5,850,352 A | 12/1998 | Moezzi et al. |
| 5,852,646 A | 12/1998 | Klotz et al. |
| 5,867,588 A | 2/1999 | Marquardt |
| 5,880,883 A | 3/1999 | Sudo |
| 5,934,288 A | 8/1999 | Avila et al. |
| 5,978,143 A | 11/1999 | Spruck |
| 5,986,662 A | 11/1999 | Argiro et al. |
| 5,993,004 A | 11/1999 | Moseley et al. |
| 5,999,165 A | 12/1999 | Matsumoto |
| 6,002,518 A | 12/1999 | Faris |
| 6,034,716 A | 3/2000 | Whiting et al. |
| 6,052,100 A | 4/2000 | Soltan et al. |
| 6,057,827 A | 5/2000 | Matthews |
| 6,066,095 A | 5/2000 | Morsy et al. |
| 6,084,937 A | 7/2000 | Tam et al. |
| 6,100,862 A | 8/2000 | Sullivan |
| 6,108,005 A | 8/2000 | Starks et al. |
| 6,115,449 A | 9/2000 | Jang et al. |
| 6,124,977 A | 9/2000 | Takahashi |
| 6,130,930 A | 10/2000 | Tam |
| 6,191,808 B1 | 2/2001 | Katayama et al. |
| 6,201,566 B1 | 3/2001 | Harada et al. |
| 6,211,884 B1 | 4/2001 | Knittel et al. |
| 6,211,927 B1 | 4/2001 | Yamazaki et al. |
| 6,220,709 B1 | 4/2001 | Heger |
| 6,225,979 B1 | 5/2001 | Taima et al. |
| 6,252,707 B1 | 6/2001 | Kleinberger et al. |
| 6,272,366 B1 | 8/2001 | Vining |
| 6,275,561 B1 | 8/2001 | Danielsson |
| 6,276,799 B1 | 8/2001 | Van Saarloos et al. |
| 6,297,799 B1 | 10/2001 | Knittel et al. |
| 6,342,378 B1 | 1/2002 | Zhang et al. |
| 6,342,878 B1 | 1/2002 | Chevassus et al. |
| 6,346,940 B1 | 2/2002 | Fukunaga |
| 6,377,230 B1 | 4/2002 | Yamazaki et al. |
| 6,407,737 B1 | 6/2002 | Zhao et al. |
| 6,413,219 B1 | 7/2002 | Avila et al. |
| 6,429,861 B1 | 8/2002 | Hossack et al. |
| 6,429,884 B1 | 8/2002 | Budz et al. |
| 6,442,417 B1 | 8/2002 | Shahidi et al. |
| 6,449,005 B1 | 9/2002 | Faris |
| 6,449,090 B1 | 9/2002 | Omar et al. |
| 6,449,309 B1 | 9/2002 | Tabata |
| 6,466,185 B2 | 10/2002 | Sullivan et al. |
| 6,476,607 B1 | 11/2002 | Dannels et al. |
| 6,487,432 B2 | 11/2002 | Slack |
| 6,490,335 B1 | 12/2002 | Wang et al. |
| 6,507,359 B1 | 1/2003 | Muramoto et al. |
| 6,532,008 B1 | 3/2003 | Guralnick |
| 6,545,650 B1 | 4/2003 | Yamada et al. |
| 6,549,803 B1 | 4/2003 | Raghavan et al. |
| 6,570,629 B1 | 5/2003 | Hirakata et al. |
| 6,580,448 B1 | 6/2003 | Stuttler |
| 6,606,091 B2 | 8/2003 | Liang et al. |
| 6,608,628 B1 | 8/2003 | Ross et al. |
| 6,676,259 B1 | 1/2004 | Trifilo |
| 6,692,441 B1 * | 2/2004 | Poland .................. G06T 15/08 600/443 |
| 6,711,231 B2 | 3/2004 | Knoplioch et al. |
| 6,734,847 B1 | 5/2004 | Baldeweg et al. |
| 6,762,794 B1 | 7/2004 | Ogino |
| 6,792,071 B2 | 9/2004 | Dewaele |
| 6,798,412 B2 | 9/2004 | Cowperthwaite |
| 6,812,929 B2 | 11/2004 | Lavelle et al. |
| 6,862,364 B1 | 3/2005 | Berestov |
| 6,885,886 B2 | 4/2005 | Bauch et al. |
| 6,947,039 B2 | 9/2005 | Gerritsen et al. |
| 7,002,619 B1 | 2/2006 | Dean et al. |
| 7,020,236 B2 | 3/2006 | Shechter |
| 7,058,156 B2 | 6/2006 | Bruder et al. |

(56) References Cited

U.S. PATENT DOCUMENTS

| | | |
|---|---|---|
| 7,113,186 B2 | 9/2006 | Kim et al. |
| RE39,342 E | 10/2006 | Starks et al. |
| 7,127,091 B2 | 10/2006 | Op De Beek |
| 7,187,420 B2 | 3/2007 | Yamazaki et al. |
| 7,190,825 B2 | 3/2007 | Yoon et al. |
| 7,193,626 B2 | 3/2007 | Otani et al. |
| 7,193,773 B2 | 3/2007 | Haisch et al. |
| 7,242,402 B1 | 7/2007 | Betting et al. |
| 7,298,372 B2 | 11/2007 | Pfister et al. |
| 7,301,510 B2 | 11/2007 | Hewitt et al. |
| 7,321,682 B2 | 1/2008 | Tooyama et al. |
| 7,324,085 B2 | 1/2008 | Balakrishnan et al. |
| 7,466,336 B2 | 12/2008 | Regan et al. |
| 7,479,933 B2 | 1/2009 | Weissman |
| 7,524,053 B2 | 4/2009 | Lipton |
| 7,604,597 B2 | 10/2009 | Murashita et al. |
| 7,605,776 B2 | 10/2009 | Satoh et al. |
| 7,643,025 B2 | 1/2010 | Lange |
| 7,647,593 B2 | 1/2010 | Matsumoto |
| 7,654,826 B2 | 2/2010 | Faulkner et al. |
| 7,715,608 B2 | 5/2010 | Vaz et al. |
| 7,773,074 B2 | 8/2010 | Arenson et al. |
| 7,786,990 B2 | 8/2010 | Wegenkittl et al. |
| 7,796,790 B2 | 9/2010 | McNutt et al. |
| 7,808,449 B2 | 10/2010 | Neidrich et al. |
| 7,822,265 B2 | 10/2010 | Berretty |
| 7,832,869 B2 | 11/2010 | Maximus et al. |
| 7,840,047 B2 | 11/2010 | Böing et al. |
| 7,907,167 B2 | 3/2011 | Vesely et al. |
| 7,957,061 B1 | 6/2011 | Connor |
| 8,049,773 B2 | 11/2011 | Ishikawa et al. |
| 8,078,000 B2 | 12/2011 | Bohm et al. |
| 8,159,526 B2 | 4/2012 | Sato et al. |
| 8,160,341 B2 | 4/2012 | Peng et al. |
| 8,165,365 B2 | 4/2012 | Bernard et al. |
| 8,175,683 B2 | 5/2012 | Roose |
| 8,199,168 B2 | 6/2012 | Virtue |
| 8,228,327 B2 | 7/2012 | Hendrickson et al. |
| 8,233,103 B2 | 7/2012 | MacNaughton et al. |
| 8,248,458 B2 | 8/2012 | Schowengerdt et al. |
| 8,289,380 B2 | 10/2012 | Kim et al. |
| 8,363,096 B1 | 1/2013 | Aguirre |
| 8,384,771 B1 | 2/2013 | Douglas et al. |
| 8,398,541 B2 | 3/2013 | DiMaio et al. |
| 8,480,234 B2 | 7/2013 | Richards |
| 8,508,583 B2 | 8/2013 | Goto |
| 8,520,024 B2 | 8/2013 | Guthrie et al. |
| 8,542,326 B2 | 9/2013 | MacNaughton et al. |
| 8,547,422 B2 | 10/2013 | Surman |
| 8,565,505 B2 | 10/2013 | Bergmans et al. |
| 8,567,954 B2 | 10/2013 | Koehler et al. |
| D692,941 S | 11/2013 | Klinar et al. |
| 8,704,879 B1 | 4/2014 | Cheng et al. |
| 8,712,137 B2 | 4/2014 | Wollenweber |
| 8,745,536 B1 | 6/2014 | Davidson |
| 8,750,450 B2 | 6/2014 | Uirici et al. |
| 8,803,946 B2 | 8/2014 | Tomita |
| 8,866,883 B2 | 10/2014 | Rohaly et al. |
| 8,885,027 B2 | 11/2014 | Yamaguchi et al. |
| 8,955,978 B2 | 2/2015 | Yanai |
| 8,964,008 B2 | 2/2015 | Bathiche |
| 8,998,417 B2 | 4/2015 | Yanai |
| 9,036,882 B2 | 5/2015 | Masumoto et al. |
| 9,077,982 B2 | 7/2015 | Rha et al. |
| 9,083,963 B2 | 7/2015 | Kamins-Naske et al. |
| 9,094,676 B1 | 7/2015 | Schutten et al. |
| 9,116,666 B2 | 8/2015 | Salter et al. |
| 9,131,913 B2 | 9/2015 | Sehnert et al. |
| 9,142,059 B1 | 9/2015 | Mallet et al. |
| 9,338,445 B2 | 5/2016 | Atkins et al. |
| 9,349,183 B1 | 5/2016 | Douglas et al. |
| 9,473,766 B2 | 10/2016 | Douglas et al. |
| 9,538,962 B1 | 1/2017 | Hannaford et al. |
| 9,677,741 B2 | 6/2017 | Hsu et al. |
| 9,691,175 B2 | 6/2017 | Rane |
| 9,736,463 B2 | 8/2017 | Gharib et al. |
| 9,769,442 B2 | 9/2017 | Shirai et al. |
| 9,980,691 B2 | 5/2018 | Douglas et al. |
| 9,986,176 B2 | 5/2018 | Moghadam |
| 10,019,812 B2 | 7/2018 | Bendall |
| 10,042,511 B2 | 8/2018 | Roe et al. |
| 10,088,686 B2 | 10/2018 | Robbins et al. |
| 10,136,124 B2 | 11/2018 | MacKenzie et al. |
| 10,297,089 B2 | 5/2019 | Buelow et al. |
| 10,373,309 B2 | 8/2019 | Thiele et al. |
| 10,417,808 B2 | 9/2019 | Noshi et al. |
| 10,492,749 B2 | 12/2019 | Boone et al. |
| 10,545,251 B2 | 1/2020 | Gesbert et al. |
| 10,795,457 B2 | 10/2020 | Douglas et al. |
| 10,936,090 B2 | 3/2021 | Douglas et al. |
| 10,942,586 B1 | 3/2021 | Douglas et al. |
| 11,016,579 B2 | 5/2021 | Douglas et al. |
| 11,036,311 B2 | 6/2021 | Douglas et al. |
| 2001/0045979 A1 | 11/2001 | Matsumoto et al. |
| 2002/0068863 A1 | 6/2002 | Slack |
| 2002/0101658 A1 | 8/2002 | Hoppenstein |
| 2002/0105602 A1 | 8/2002 | Pan |
| 2002/0112237 A1 | 8/2002 | Kelts |
| 2002/0113868 A1 | 8/2002 | Park |
| 2002/0183607 A1 | 12/2002 | Bauch et al. |
| 2003/0020809 A1 | 1/2003 | Gibbon et al. |
| 2003/0026474 A1 | 2/2003 | Yano |
| 2003/0107644 A1 | 6/2003 | Choi |
| 2003/0194119 A1 | 10/2003 | Manjeshwar et al. |
| 2003/0204364 A1 | 10/2003 | Goodwin et al. |
| 2003/0218720 A1 | 11/2003 | Morita et al. |
| 2004/0054248 A1 | 3/2004 | Kimchy et al. |
| 2004/0059214 A1 | 3/2004 | Tomoda et al. |
| 2004/0070584 A1 | 4/2004 | Pyo et al. |
| 2004/0082846 A1 | 4/2004 | Johnson et al. |
| 2004/0096799 A1 | 5/2004 | Hughes et al. |
| 2004/0174605 A1 | 9/2004 | Olsson |
| 2004/0204644 A1 | 10/2004 | Tsougarakis et al. |
| 2004/0208358 A1 | 10/2004 | Tooyama et al. |
| 2004/0223636 A1 | 11/2004 | Edie et al. |
| 2004/0238732 A1 | 12/2004 | State et al. |
| 2004/0246269 A1 | 12/2004 | Serra et al. |
| 2004/0254454 A1 | 12/2004 | Kockro |
| 2005/0017938 A1 | 1/2005 | O'Donnell et al. |
| 2005/0030621 A1 | 2/2005 | Takahashi et al. |
| 2005/0055118 A1 | 3/2005 | Nikolskiy et al. |
| 2005/0062684 A1 | 3/2005 | Geng |
| 2005/0065423 A1 | 3/2005 | Owen |
| 2005/0065424 A1 | 3/2005 | Shah et al. |
| 2005/0096530 A1 | 5/2005 | Daw et al. |
| 2005/0110791 A1 | 5/2005 | Krishnamoorthy et al. |
| 2005/0148848 A1 | 7/2005 | Guang et al. |
| 2005/0151152 A1 | 7/2005 | Miller et al. |
| 2005/0151730 A1 | 7/2005 | Lobregt |
| 2005/0152591 A1 | 7/2005 | Kiraly et al. |
| 2005/0208449 A1 | 9/2005 | Abolfathl et al. |
| 2005/0228250 A1 | 10/2005 | Bitter et al. |
| 2005/0244050 A1 | 11/2005 | Nomura et al. |
| 2005/0245803 A1 | 11/2005 | Glen, Jr. et al. |
| 2005/0278408 A1 | 12/2005 | Matsumoto |
| 2005/0283063 A1 | 12/2005 | Besson et al. |
| 2005/0285844 A1 | 12/2005 | Morita et al. |
| 2006/0013472 A1 | 1/2006 | Kagitani |
| 2006/0026533 A1 | 2/2006 | Napoli et al. |
| 2006/0033992 A1 | 2/2006 | Solomon |
| 2006/0056680 A1 | 3/2006 | Stutsman et al. |
| 2006/0056726 A1 | 3/2006 | Fujiwara et al. |
| 2006/0058605 A1 | 3/2006 | Deischinger et al. |
| 2006/0077204 A1 | 4/2006 | Pfister et al. |
| 2006/0079755 A1 | 4/2006 | Stazzone et al. |
| 2006/0109753 A1 | 5/2006 | Fergason |
| 2006/0120583 A1 | 6/2006 | Dewaele |
| 2006/0171028 A1 | 8/2006 | Oikawa et al. |
| 2006/0173338 A1 | 8/2006 | Ma et al. |
| 2006/0177133 A1 | 8/2006 | Kee |
| 2006/0210111 A1 | 9/2006 | Cleveland et al. |
| 2006/0210147 A1 | 9/2006 | Sakaguchi |
| 2006/0227103 A1 | 10/2006 | Koo et al. |
| 2006/0232665 A1 | 10/2006 | Schowengerdt et al. |

(56) References Cited

U.S. PATENT DOCUMENTS

| | | |
|---|---|---|
| 2006/0238441 A1 | 10/2006 | Benjamin et al. |
| 2006/0239523 A1 | 10/2006 | Stewart et al. |
| 2006/0268104 A1 | 11/2006 | Cowan et al. |
| 2006/0279569 A1 | 12/2006 | Acosta et al. |
| 2006/0286501 A1 | 12/2006 | Chishti et al. |
| 2007/0021738 A1 | 1/2007 | Hasser et al. |
| 2007/0035830 A1 | 2/2007 | Matveev et al. |
| 2007/0040854 A1 | 2/2007 | Lievin et al. |
| 2007/0053562 A1 | 3/2007 | Reinhardt et al. |
| 2007/0058249 A1 | 3/2007 | Hirose et al. |
| 2007/0085902 A1 | 4/2007 | Walker et al. |
| 2007/0103459 A1 | 5/2007 | Stoval, III et al. |
| 2007/0115204 A1 | 5/2007 | Budz et al. |
| 2007/0116357 A1 | 5/2007 | Dewaele |
| 2007/0118408 A1 | 5/2007 | Mahesh et al. |
| 2007/0146325 A1 | 6/2007 | Poston et al. |
| 2007/0147671 A1 | 6/2007 | Di Vincenzo et al. |
| 2007/0165927 A1 | 7/2007 | Muradyan et al. |
| 2007/0167801 A1 | 7/2007 | Webler et al. |
| 2007/0188520 A1 | 8/2007 | Finley et al. |
| 2007/0206155 A1 | 9/2007 | Lipton |
| 2007/0237369 A1 | 10/2007 | Brunner et al. |
| 2007/0274585 A1 | 11/2007 | Zhang et al. |
| 2007/0279435 A1 | 12/2007 | Ng et al. |
| 2007/0279436 A1 | 12/2007 | Ng et al. |
| 2007/0285774 A1 | 12/2007 | Merrirt et al. |
| 2008/0002262 A1 | 1/2008 | Chirieleison |
| 2008/0025584 A1 | 1/2008 | Kunz |
| 2008/0033240 A1 | 2/2008 | Hoffman et al. |
| 2008/0037843 A1 | 2/2008 | Fu et al. |
| 2008/0044069 A1 | 2/2008 | DuGal |
| 2008/0055305 A1 | 3/2008 | Blank et al. |
| 2008/0055310 A1 | 3/2008 | Mitchell et al. |
| 2008/0062173 A1 | 3/2008 | Tashiro |
| 2008/0088621 A1 | 4/2008 | Grimaud et al. |
| 2008/0094398 A1 | 4/2008 | Ng et al. |
| 2008/0100612 A1 | 5/2008 | Dastmalchi et al. |
| 2008/0117233 A1 | 5/2008 | Mather et al. |
| 2008/0154952 A1 | 6/2008 | Waldlnger et al. |
| 2008/0267499 A1 | 10/2008 | Deischinger et al. |
| 2008/0267527 A1 | 10/2008 | Berretty |
| 2008/0281182 A1 | 11/2008 | Rabben et al. |
| 2008/0291268 A1 | 11/2008 | Beretty |
| 2008/0297434 A1 | 12/2008 | Ablleah |
| 2009/0016491 A1 | 1/2009 | Li |
| 2009/0034684 A1 | 2/2009 | Bernard et al. |
| 2009/0040227 A1 | 2/2009 | Vrba |
| 2009/0051685 A1 | 2/2009 | Takagi et al. |
| 2009/0080765 A1 | 3/2009 | Bernard et al. |
| 2009/0119609 A1 | 5/2009 | Matsumoto |
| 2009/0147073 A1 | 6/2009 | Getty |
| 2009/0217209 A1 | 8/2009 | Chen et al. |
| 2009/0219283 A1 | 9/2009 | Hendrickson et al. |
| 2009/0219383 A1 | 9/2009 | Passmore |
| 2009/0231697 A1 | 9/2009 | Marcus et al. |
| 2009/0232275 A1 | 9/2009 | Spartiotis et al. |
| 2009/0237492 A1 | 9/2009 | Kikinis et al. |
| 2009/0244267 A1 | 10/2009 | Yuan et al. |
| 2009/0278917 A1 | 11/2009 | Dobbins et al. |
| 2009/0282429 A1 | 11/2009 | Olsson et al. |
| 2009/0304232 A1 | 12/2009 | Tsukizawa |
| 2009/0324052 A1 | 12/2009 | Nowinski |
| 2010/0045783 A1 | 2/2010 | State et al. |
| 2010/0085423 A1 | 8/2010 | Lange |
| 2010/0194861 A1 | 8/2010 | Hoppenstein |
| 2010/0201785 A1 | 8/2010 | Lantin |
| 2010/0231705 A1 | 9/2010 | Yahav et al. |
| 2010/0246911 A1 | 9/2010 | Rabben et al. |
| 2011/0026808 A1 | 2/2011 | Kim et al. |
| 2011/0043644 A1 | 2/2011 | Munger et al. |
| 2011/0063576 A1 | 3/2011 | Redmann et al. |
| 2011/0107270 A1 | 5/2011 | Wang et al. |
| 2011/0109620 A1 | 5/2011 | Hong et al. |
| 2011/0141246 A1 | 6/2011 | Schwartz et al. |
| 2011/0194728 A1 | 8/2011 | Kutcka et al. |
| 2011/0227910 A1 | 9/2011 | Ying et al. |
| 2011/0228051 A1 | 9/2011 | Dedoglu et al. |
| 2011/0254845 A1 | 10/2011 | Oikawa et al. |
| 2011/0273543 A1 | 11/2011 | Ushio et al. |
| 2011/0279450 A1 | 11/2011 | Seong et al. |
| 2011/0293161 A1 | 12/2011 | Yi et al. |
| 2012/0008734 A1 | 1/2012 | Thomson et al. |
| 2012/0008735 A1 | 1/2012 | Maurer et al. |
| 2012/0013711 A1 | 1/2012 | Tamir et al. |
| 2012/0019636 A1 | 1/2012 | Gefen et al. |
| 2012/0038631 A1 | 2/2012 | Mayhew et al. |
| 2012/0056998 A1 | 3/2012 | Kang et al. |
| 2012/0071755 A1 | 3/2012 | Zheng et al. |
| 2012/0075293 A1 | 3/2012 | Kuwabara et al. |
| 2012/0113235 A1 | 5/2012 | Shintani |
| 2012/0120202 A1 | 5/2012 | Yoon et al. |
| 2012/0120207 A1 | 5/2012 | Shimazaki et al. |
| 2012/0127284 A1 | 5/2012 | Bar-Zeev et al. |
| 2012/0162219 A1 | 6/2012 | Kobayashi et al. |
| 2012/0190439 A1 | 7/2012 | Nourbakhsh |
| 2012/0190967 A1 | 7/2012 | Nahm |
| 2012/0206665 A1 | 8/2012 | Sakai et al. |
| 2012/0209106 A1 | 8/2012 | Liang et al. |
| 2012/0215218 A1 | 8/2012 | Lipani |
| 2012/0224755 A1 | 9/2012 | Wu |
| 2012/0229595 A1 | 9/2012 | Miller |
| 2012/0242569 A1 | 9/2012 | Hamagishi |
| 2012/0269424 A1 | 10/2012 | Ebata et al. |
| 2012/0287361 A1 | 11/2012 | Sugihara |
| 2012/0306849 A1 | 12/2012 | Steen |
| 2013/0002646 A1 | 1/2013 | Lin et al. |
| 2013/0003020 A1 | 1/2013 | Koehler et al. |
| 2013/0057830 A1 | 3/2013 | Tsai et al. |
| 2013/0070984 A1 | 3/2013 | Shirasaka et al. |
| 2013/0076876 A1 | 3/2013 | Shimotani et al. |
| 2013/0141552 A1 | 6/2013 | Kwon |
| 2013/0176566 A1 | 7/2013 | Mitchell et al. |
| 2013/0182085 A1 | 7/2013 | Ziarati |
| 2013/0242063 A1 | 9/2013 | Matsumoto |
| 2013/0245375 A1 | 9/2013 | DiMaio et al. |
| 2013/0251242 A1 | 9/2013 | Suzuki et al. |
| 2013/0278727 A1 | 10/2013 | Tamir et al. |
| 2013/0335417 A1 | 12/2013 | McQueston et al. |
| 2014/0051988 A1 | 2/2014 | Lautenschlager |
| 2014/0063376 A1 | 3/2014 | Tsang et al. |
| 2014/0065663 A1 | 3/2014 | Vasquez et al. |
| 2014/0176685 A1 | 6/2014 | Oikawa et al. |
| 2014/0210965 A1 | 7/2014 | Goodman et al. |
| 2014/0253698 A1 | 9/2014 | Evans et al. |
| 2014/0253699 A1 | 9/2014 | Schafer et al. |
| 2014/0308624 A1 | 10/2014 | Lee et al. |
| 2014/0340400 A1 | 11/2014 | Takeguchi et al. |
| 2014/0347726 A1 | 11/2014 | Yang et al. |
| 2015/0077713 A1 | 3/2015 | Drumm |
| 2015/0110374 A1 | 4/2015 | Traughber et al. |
| 2015/0139514 A1 | 5/2015 | Mohr et al. |
| 2016/0038248 A1 | 2/2016 | Bharadwaj et al. |
| 2016/0129637 A1 | 5/2016 | Zhou et al. |
| 2016/0287201 A1 | 10/2016 | Bergtholdt et al. |
| 2016/0302895 A1 | 10/2016 | Rohaly et al. |

FOREIGN PATENT DOCUMENTS

| | | |
|---|---|---|
| DE | 19534750 A1 | 3/1997 |
| DE | 102011080588 A1 | 2/2013 |
| EP | 0571827 A | 12/1993 |
| EP | 0592652 B1 | 9/1997 |
| EP | 0918242 A1 | 5/1999 |
| EP | 1056049 A2 | 11/2000 |
| EP | 0970589 B1 | 8/2004 |
| EP | 1683485 A1 | 7/2006 |
| EP | 1791087 A | 5/2007 |
| EP | 1843296 A1 | 10/2007 |
| FR | 2838598 B1 | 10/2004 |
| JP | H 09-205660 | 8/1997 |
| JP | H 11-232010 A | 8/1999 |
| JP | 2000-333950 A | 12/2000 |
| JP | 2001-504603 A | 4/2001 |
| JP | 2002-330958 A | 11/2002 |

(56) References Cited

FOREIGN PATENT DOCUMENTS

| | | |
|---|---|---|
| JP | 2005-130309 A | 5/2005 |
| JP | 2005-521960 A | 7/2005 |
| JP | 2006-113088 A | 4/2006 |
| JP | 3816599 B2 | 6/2006 |
| JP | 2008-220406 A | 9/2008 |
| JP | 2009-000167 A | 1/2009 |
| JP | 2009-018048 A | 1/2009 |
| JP | 2009-022476 A | 2/2009 |
| JP | 2009-515404 A | 4/2009 |
| JP | 4319165 B2 | 6/2009 |
| JP | 4519898 B2 | 5/2010 |
| JP | 2012-105796 A | 6/2012 |
| JP | 2012-142846 A | 7/2012 |
| JP | 2013-538360 A | 10/2013 |
| JP | 2014-222459 A | 11/2014 |
| JP | 2015-036084 A | 2/2015 |
| KR | 10-2004-0076846 A | 9/2004 |
| KR | 10-2006-0085596 A | 7/2006 |
| KR | 10-0659327 B1 | 12/2006 |
| KR | 10-2007-0082138 A | 8/2007 |
| KR | 10-2011-0125416 A | 11/2011 |
| KR | 10-1083808 B1 | 11/2011 |
| KR | 10-2012-0051065 A | 5/2012 |
| KR | 10-1162053 B1 | 7/2012 |
| KR | 10-2014-0048994 A | 4/2014 |
| WO | WO 95/00872 | 1/1995 |
| WO | WO 97/00482 | 1/1997 |
| WO | WO 97/46029 | 12/1997 |
| WO | WO 99/23586 | 5/1999 |
| WO | WO 01/005161 | 1/2001 |
| WO | WO 03/010977 | 2/2003 |
| WO | WO 03/083781 | 10/2003 |
| WO | WO 03/100542 | 12/2003 |
| WO | WO 2005/062629 | 7/2005 |
| WO | WO 2006/038744 | 4/2006 |
| WO | WO 2007/052216 | 5/2007 |
| WO | WO 2007/059477 | 5/2007 |
| WO | WO 2007/063442 | 6/2007 |
| WO | WO 2009/076303 | 6/2009 |
| WO | WO 2011/031315 | 3/2011 |
| WO | WO 2011/160200 | 12/2011 |
| WO | WO 2012/030091 | 3/2012 |
| WO | WO 2012/101395 | 8/2012 |
| WO | WO 2012/144453 | 10/2012 |
| WO | WO 2013/011035 | 1/2013 |
| WO | WO 2015/069049 | 5/2015 |
| WO | 2017066373 A1 | 4/2017 |

OTHER PUBLICATIONS

U.S. Appl. No. 60/735,458, filed Nov. 11, 2005, Murphy et al.
U.S. Appl. No. 60/764,508, filed Feb. 2, 2006, Murphy et al.
U.S. Appl. No. 60/835,852, filed Aug. 4, 2006, Anderson et al.
U.S. Appl. No. 60/842,377, filed Sep. 6, 2006, Nowinski.
U.S. Appl. No. 60/854,872, filed Oct. 27, 2006, Dastmalchi et al.
Azuma, Ronald T. "A Survey of Augmented Reality" In Presence: Teleoperators and Virtual Environments 6, 4 (Aug. 1997) pp. 355-385.
Bakalash, Reuven et al. "Medicube: A 3D Medical Imaging Architecture" Computer &Graphics vol. 13, No. 2, pp. 151-157; 1989.
By the Editors of Electronic Gaming Monthly "1993 Video Game Preview Guide" 1993.
Cakmaki, Ozan et al. "Head-Worn Displays: A Review" Journal of Display Technology, vol. 2, No. 3, Sep. 2006.
Calhoun, Paul S. et al. "Three-Dimensional Volume Rendering of Spiral CT Data: Theory and Method" Radio Graphics; vol. 19, No. 3; May-Jun. 1999.
CBR Staff Writer "Sense8 Launches World Up, Virtual Reality Tool" CBR; https://www.cbronline.com; Sep. 8, 1995.
Cevidanes, Lucia H.S., et al., "Image Analysis and Superimposition of 3-Dimensional Cone-Beam Computed Tomography Models" The American Association of Orthodontists; 2006; 8pages.
Cochrane, Nathan "VFX-1 Virtual Reality Helmet by Forte" Game Bytes Magazine; 1994.
D'Orazio, Dante et al. "Valve's VR Headset is Called the Vive and it's Made by HTC" The Verge; https://www.theverge/com/2015/3/1/8127445/htc-vive-valve-vr-headset; Mar. 1, 2015.
Digest of Papers "First International Symposium on Wearable Computers" IEEE Computer Society Technical Committee on Fault Tolerant Computing; Cambridge, MA; Oct. 13-14, 1997 (5 pages).
Digest of Papers "Second International Symposium on Wearable Computers" IEEE Computer Society Technical Committee on Fault Tolerant Computing; Pittsburgh, PA; Oct. 19-20, 1998 (6 pages).
Doneus, Michael et al. "Anaglyph Images—Still A Good Way to Look at 3D-Objects?" Oct. 1999.
Douglas, David B. et al. "Augmented Reality Imaging System: 3D Viewing of a Breast Cancer" J Nat Sci, 2016;2(9).
Douglas, David B. et al. "Augmented Reality: Advances in Diagnostic Imaging: Multimodal Technologies and Interaction" 2017; 1(4):29.
Douglas, David B. et al. "D3D Augmented Reality Imaging System: Proof of Concept in Mammography" Med Devices (Auckl), 2016; 9:277-83.
Edirisinghe, E.A. et al. "Stereo Imaging, An Emerging Technology" Jan. 2000.
Engel, K., et al. "Combining Local and Remote Visualization Techniques for Interactive Volume Rendering in Medical Applications" Proceedings Visualization 2000. VIS 2000 (Cat. No. 00CH37145), Salt Lake City, UT, USA, 2000, pp. 449-452.
Erickson, Bradley J. "A Desktop Computer-Based Workstation for Display and Analysis of 3-and 4-Dimensional Biomedical Images" Computer Methods and Programs in Biomedicine, 30; pp. 97-110; 1989.
Fisher, Scott S. "Portfolio of Work: Environmental Media Project" Graduate School of Media and Governance, Keio University, Tokyo, Japan 1999-Current.
Fisher, Scott S. "Portfolio of Work: Menagerie" Telepresence Research, Inc. San Francisco, CA 1993.
Fisher, Scott S. "Portfolio of Work: NASA VIEWlab" NASA Ames Research Center, Mountain View CA 1985-90.
Fisher, Scott S. "Portfolio of Work: Stereoscopic Workstation" Architecture Machine Group, MIT, Cambridge, MA 1981.
Fisher, Scott S. "Portfolio of Work: Telepresence Mobile Robot" Telepresence Research, Inc., San Francisco, CA 1991.
Fisher, Scott S. "Portfolio of Work: Viewpoint Dependent Imaging" Architecture Machine Group, MIT, Cambridge, MA 1981.
Fisher, Scott S. Portfolio of Work: Virtual Brewery Adventure: Telepresence Research, Inc., San Francisco, CA 1994.
Fisher, Scott S. "Portfolio of Work: Virtual Explorer" University of California, San Diego, CA 1998.
Fisher, Scott S. et al. "Virtual Interface Environment Workstations" Proceedings of the Human Factors Society—32nd Annual Meeting—1988.
Fisher, Scott S. "Portfolio of Work: VRML Projects" Telepresence Research, Inc., San Francisco, CA 1996.
Foley et al. "The Systems Programming Series: Computer Graphics: Principles and Practice Second Edition" Addison-Wesley Publishing Company; 1990.
Fuhrmann, A.L. et al. "Distributed Software-Based Volume Visualization in a Virtual Environment" The Eurographics Association and Blackwell Publishing; vol. 0, No. 0, pp. 1-11; 1981.
Galton, N. "Fast Inspection of Contents of a Volume of 3D Data" IBM Technical Disclosure Bulletin; ip.com: Feb. 1, 1994 (3 pages).
Goodsitt, Mitchel M. et al. "Stereomammography: Evaluation of Depth Perception using a Virtual 3D Cursor" Med. Phys. 27 (6), Jun. 2000.
Haker, Steven et al. "Nondistorting Flattening Maps and the 3-D Visualization of Colon CT Images" IEEE Transactions of Medical Imaging; vol. 19, No. 7; Jul. 2000; 665-670.
He, Changming "Volume Visualization in Projection-Based Virtual Environments: Interaction and Exploration Tools Design and Evaluation" Griffith University; 2011.
Heuser, John E. "Membrane Traffic in Anaglyph Stereo" Munksgaard International Publishers; Traffic 2000, vol. 1, 35-37.

(56) References Cited

OTHER PUBLICATIONS

Hinckley, Ken "Haptic issues forVirtual Manipulation" A Dissertation Presented to the Faculty of the School of Engineering and Applied Science at the University of Virginia; Dec. 1996.

Hinckley, Ken, et al. "New Applications for the Touchscreen in 2D and 3D Medical Imaging Workstations" Proc. SPIE Medical Imaging '95: Image Display, SPIE vol. 2431, pp. 110-118.

Hui, Y.W. et al. "3D Cursors for Volume Rendering Applications" EEE Conference on Nuclear Science Symposium and Medical Imaging, Orlando, FL, USA, 1992, pp. 1243-1245 vol. 2.

Hong, Lichan et al. "Reconstruction and Visualization of 3D Models of Colonic Surface" IEEE Transactions on Nuclear Science, vol. 44, No. 3, Jun. 1997.

IBM "Fast inspection of Contents of a Volume of 3D Data" IBM Technical Disclosure Bulletin; Feb. 1, 1994; vol. 37, Issue 2A.

IEEE 1998 Virtual Reality Annual International Symposium IEEE Computer Society; Atlanta, GA; Mar. 14-18, 1998 (8 pages).

Interrante, Victoria et al. "Strategies for Effectively Visualizing 3D Flow with Volume LIC" IEEE Visualization Conference; 1997; pp. 1-5.

Kaluszka, Aaron "3DS North American Price, Date, Colors Set" NintendoWorld Report; Jan. 19, 2011.

Kancherla, Anantha R. et al. "A Novel Virtual Reality Tool For Teaching Dynamic 3D Anatomy" Conference Paper; Jan. 1995.

Kapur, Ajay et al. "Combination of Digital Mammography with Semi-Automated 3D Breast Ultrasound" NIH Public Access; Author Manuscript; Technol Cancer Res Treat, 3(4); 325-334; Aug. 2004.

Kato, Hirokazu et al. "Marker Tracking and HMD Calibration for a Video-Based Augmented Reality Conferencing System" IWAR '99: Proceedings of the 2nd IEEE and ACM International Workshop on Augmented Reality; Oct. 1999.

Kaufman, A., et a. "Real-Time Volume Rendering" International Journal of Imaging Systems and Technology, special issue on 3D Imaging; 2000.

Klein, GJ et al. "A 3D Navigational Environment for Specifying Positron Emission Tomography Volumes-of-Interest" 1995 IEEE Nuclear Science Symposium and Medical Imaging Conference Record, San Francisco, CA, USA, 1995, pp. 1452-1455 vol. 3.

Kniss, Joe et al. "Interactive Texture-Based Volume Rendering for Large Data Sets" IEEE Computer Graphics and Applications; Jul./Aug. 2001.

Kok, Arjan J.F. et al. "A Multimodal Virtual Reality Interface for 3D Interaction with VTK" Knowledge and Information Systems; 2007.

Krapichler, Christian et al. "VR interaction Techniques for Medical Imaging Applications" Computer Methods and Programs in Biomedicine 56; pp. 65-74; 1998.

Kratz, Andrea et al. "GPU-Based High-Quality Volume Rendering for Virtual Environments" Oct. 2006.

Kratz, Andrea "Integration of Hardware Volume Renderer into a Virtual Reality Application" Universitat Koblenz Landau; Oct. 2005.

Kreeger, Kevin et al. "Interactive vol. Segmentation with the PAVLOV Architecture" Proceedings 1999 IEEE Parallel Visualization and Graphics Symposium (Cat. No. 99EX381), San Francisco, CA, USA, 1999, pp. 61-119.

Kress, Bernard et al. "Speckle Reduction Technique for Laser Based Automotive Head Up Display (HUD) Projectors" Proceedings vol. 8026, Photonic Applications for Aerospace, Transportation, and Harsh Environment II; 80260P (2011) https://doi.org/10.1117/12.886536; May 26, 2011.

Laplante, Philip A. "Second Edition Comprehensive Dictionary of Electrical Engineering" Taylor & Francis; 2005; p. 165.

Li, Yanhong et al. "Tinkerbell—A Tool for Interactive Segmentation of 3D Data" Journal of Structural Biology 120, 266-275; 1997.

Lima, Luis Alberto et al. "Virtual Seismic Interpretation" IEEE XI SIBGRAPI Proceedings, Oct. 1998.

Löbbert, Sebastian et al. "Visualisation of Two-Dimensional Volumes" 2004.

Loh, Yong Chong et al. "Surgical Planning System with Real-Time Volume Rendering" Proceedings International Workshop on Medical Imaging and Augmented Reality, Shatin, Hong Kong, China, 2001, pp. 259-261.

Lorensen, William E. et al. "Marching Cubes: A High Resolution 3D Surface Construction Algorithm" SIGGRAPH '87: Proceedings of the 14th annual conference on Computer graphics and interactive techniques Aug. 1987.

Marescaux, Jacques et al. "Augmented-Reality-Assisted Laparoscopic Adrenalectomy" Journal of American Medical Association; vol. 292, No. 18; Nov. 10, 2004.

Martin, RW et al. "Stereographic Viewing of 3D Ultrasound Images: A Novelty ora Tool?" 1995 IEEE Ultrasonics Symposium; IEEE Press 1431-1434.

McAllister, David F. "Display Technology: Stereo & 3D Display Technologies" Mar. 2003.

McKenna, Michael et al. "Three Dimensional Visual Display Systems for Virtual Environments" The Massachusetts Institute of Technology; Presence, vol. 1, No. 4, Fall 1992.

Mellott "Cybermaxx Virtual Reality Helmet" Mellott's VR; https://www.mellottsvrpage.com/index/php/cybermaxx-virtual-reality-helmet/; Jan. 26, 2021.

Moeller, D.P.F "Mathematical and Computational Modeling and Simulation: Fundamentals and Case Studies" Springer-Verlag Berlin Heidelber; 2004.

Moreira, Dilvan A. et al. "3D Markup of Radiological Images in ePAD, a Web-Based Image Annotation Tool" 2015 IEEE 28th International Symposium on Computer-Based Medical Systems; 2015.

NASA "The Virtual Interface Environment Workstation (VIEW)" Partnership with VPL Research, Inc.; https://www.nasa.gov/ames/spinoff/new_continent_of_ideas/; 1990.

Osorio, Angel et ai. "A New PC Based on Software to Take and Validate Clinical Decisions for Colorectal Cancer using Metric 3D Images Segmentations" https://dx.doi.org/10.1594/ecr2010/C-1071; 10.1594/ecr2010/C-1071; 2010.

Peterson, Christine M. et al. "Volvulus of the Gastrointestinal Tract: Appearances at Multi-Modality Imaging" Radiographics; vol. 29, No. 5; Sep.-Oct. 2009; pp. 1281-1293.

Piekarski, Wayne "interactive 3D Modelling in Outdoor Augmented Reality Worlds" Wearable Computer Lab, School of Computer and Information Science; The University of South Australia; Feb. 2004.

PlayStation "Announcing the Price and Release Date for PlayStation VR" Available at https://www.youtube.com/watch?v=wZ57CI3Nq60; Mar. 15, 2016.

Popescu, Voicu et al. "Three-Dimensional Display Rendering Acceleration Using Occlusion Camera Reference Images" Journal of Display Technology, vol. 2, No. 3, Sep. 2006.

Radeva, Nadezhda et al. "Generalized Temporal Focus+Context Framework for Improved Medical Data Exploration" Society for Imaging Informatics in Medicine; Jan. 8, 2014.

Robb, R.A., et al. "A Workstation for Interactive Display and Quantitative Analysis of 3-D and 4-D Biomedical images" Biodynamics Research Unit, IEEE, 1986.

Robb, R.A. et al. "Interactive Display and Analysis of 3-D Medical Images" IEEE Transactions on Medical Imaging, vol. 8, No. 3, Sep. 1989.

Rosenberg, Adam "Hands-On with Oculus Rift, John Carmack's Virtual Reality Goggles" G4 Media, LLC; Jun. 14, 2012.

Schmalstieg, Dieter et al. "The Studierstube Augmented Reality Project" https://arbook.icg.tugraz.at/schmalstieg/Schmalstieg_045.pdf; 2005.

ScienceDaily "FDA Approves New Robotic Surgery Device" ScienceDaily; Food and Drug Administration; Jul. 17, 2000.

Skoglund, T. et al. "3D Reconstruction of Biological Objects from Sequential Image Planes—Applied on Cerebral Cortex from CAT" Computerized Medical imaging and Graphics; vol. 17, No. 3, pp. 165-174; 1993.

Soler, L., et al. "Virtual Reality and Augmented Reality in Digestive Surgery" Proceedings of the Third IEEE and ACM International Symposium on Mixed and Augmented Reality; 2004.

(56) References Cited

OTHER PUBLICATIONS

Soler, Luc et al. "Virtual Reality, Augmented Reality, and Robotics Applied to Digestive Operative Procedures: From in Vivo Animal Preclinical Studies to Clinical use" Proceedings of SPIE; 2006.
Sony "Sony Global—Product & Technology Milestones—Projector" https://www.sony.net/SonyInfo/CorporateInfo/History/sonyhistory-n.html; printed Feb. 23, 2021.
Sony "Projector Head Mounted Display" Sony Global—Product & Technology Milestones-Projector Head Mounted Display; https://www.sony.net/SonyInfo/CorporateInfo/History/sonyhistory-n.html; Jan. 26, 2021.
Steinicke, Frank et al. "Towards Applicable 3D User Interfaces for Everyday Working Environments" Conference Paper; Sep. 2007.
Storey, Neil et al. "Interactive Stereoscopic Computer Graphic Display Systems" Proc. Ineract '84; pp. 163-168; Sep. 4-7, 1984.
Subramanian, Sriram "Tangible Interfaces for Volume Navigation" CIP-Data Library Technische University Eindhoven; 2004.
Sutherland, Ivan E. "A Head-Mounted Three Dimensional Display" Fall Join Computer Conference, 1968.
The Computer Chronicles "Virtual Reality" available at https://www.youtube.com/watch?v=:wfHMSqQKg6s; 1992.
Tresens, Marc Antonijuan et al. "Hybrid-Reality: A Collaborative Environment for Biomedial Data Exploration Exploiting 2-D and 3-D Correspondence" Studies in Health Technology and Informatics; Feb. 2004.
Ultrasound Visualization Research "UNC Ultrasound/Medical Augmented Reality Research: Augmented Reality Technology" https://www.cs.unc.edu/Research/US/; Jun. 15, 2000.
Vanacken, Lode et al. "Exploring the Effects of Environment Density and Target Visibility on Object Selection in 3D Virtual Environments" IEEE Symposium on 3D User Interfaces Mar. 10-11, 2007.
Vidal, F. P. et al. "Principles and Applications of Medical Virtual Environments" Eurographics 2004.
V-Rtifacts "Retrospective Photo Review of Forte VFX1 Virtual Reality System" https://wwvrtifacts.com/retrospective-photo-review-of-forte-vfx1-virtual-reality-system/: Jan. 26, 2021.
V-Rtifacts "Teardown—Virtual Research V6: Head Mounted Displays, How-To; Teardowns; Tutorials, Stereoscopic 3D, VR Companies" https://vrtifacts.com/teardown-virtual-research-v6/; printed Jan. 26, 2021.
Ware, Colin et al., "Selection Using a One-Eyed Cursor in a Fish Tank VR Environment" Faculty of Computer Science, University of new Brunswick; Apr. 20, 2000.
Wikipedia "MechWarrior 31st Century Combat" https://en.wikipedia.org/wiki/MechWarrior_2:_31st_Century_Combat; Jan. 26, 2021.
Wikipedia "Virtual Boy" https://en.wikipedia.org/wiki/Virtual_Boy; Jan. 11, 2021.
Wikipedia "VPL Research" https://en.wikipedia.org/wiki/VPL_Research; Jan. 22, 2021.
Wither, Jason et al. "Pictorial Depth Cues for Outdoor Augmented Reality" Ninth IEEE International Symposium on Wearable Computers (ISWC'05), Osaka, 2005, pp. 92-99.
Wong, Terence Z. et al. "Stereoscopically Guided Characterization of Three-Dimensional Dynamic MR Images of the Breast" Radiology, 1996; 198:288-291.
Yushkevich, Paul A et al. "User-Guided 3D Active Contour Segmentation of Anatomical Structures: Significantly Improved Efficiency and Reliability" NeuroImage 31; 1116-1128; 2006.
Zhai, Shumin et al. "The Partial Occlusion Effect: Utilizing Semi-Transparency in 3D Human Computer Interaction" ACM Transactions on Computer-Human Interaction, 3(3), 254-284; 1996.
Office Action for U.S. Appl. No. 11/941,578, dated Sep. 29, 2011.
Office Action for U.S. Appl. No. 11/941,578, dated Feb. 22, 2012.
Notice of Allowance for U.S. Appl. No. 11/941,578, dated Dec. 21, 2012.
Office Action for U.S. Appl. No. 12/176,569, dated Apr. 4, 2012.
Office Action for U.S. Appl. No. 12/176,569, dated Oct. 26, 2012.
Office Action for U.S. Appl. No. 12/176,569, dated Jul. 15, 2014.
Office Action for U.S. Appl. No. 12/176,569, dated Feb. 5, 2015.
Notice of Allowance for U.S. Appl. No. 12/176,569, dated May 29, 2015.
Office Action for U.S. Appl. No. 14/313,398 dated Sep. 25, 2015.
Office Action for U.S. Appl. No. 14/313,398 dated May 12, 2016.
Notice of Allowance for U.S. Appl. No. 14/313,398 dated Jul. 15, 2016.
Office Action for U.S. Appl. No. 14/877,442 dated Jul. 14, 2017.
Office Action for U.S. Appl. No. 14/877,442 dated Dec. 5, 2017.
Notice of Allowance for U.S. Appl. No. 14/87/,442 dated Apr. 5. 2018.
Office Action for U.S. Appl. No. 15/878,463 dated Jun. 13, 2019.
Office Action for U.S. Appl. No. 15/878,463 dated Sep. 24, 2019.
Office Action for U.S. Appl. No. 15/878,463 dated Feb. 24, 2020.
Notice of Allowance for U.S. Appl. No. 15/878,463 dated Aug. 10, 2020.
Notice of Allowance for U.S. Appl. No. 17/021,548 dated Jan. 13. 2021.
Notice of Allowance for U.S. Appl. No. 17/095,411 dated Feb. 2, 2021.
Notice of Allowance for U.S. Appl. No. 17/122,518 dated Mar. 8, 2021.
Notice of Allowance for U.S. Appl. No. 17/122,549 dated Mar. 3, 2021.
Documents filed with U.S. District Court Proceedings for *D3D Technologies, Inc.* v. *Microsoft Corporation*; U.S. District Court, Middle District of Florida Orlando Division; Civil Action No. 6:20-cv-01699-GAP-DCI; Includes publicly available documents filed from Sep. 16, 2020-Oct. 6, 2020; (991 pages).
Documents filed with U.S. District Court Proceedings for *D3D Technologies, Inc.* v. *Microsoft Corporation*; U.S. District Court, Middle District of Florida Orlando Division; Civil Action No. 6:20-cv-01699-GAP-DCI; Includes publicly available documents filed from Nov. 9, 2020-Jan. 4, 2021; (1,536 pages).
Documents filed with U.S. District Court Proceedings for *D3D Technologies, Inc.* v. *Microsoft Corporation*; U.S. District Court, Middle District of Florida Orlando Division; Civil Action No. 6:20-cv-01699-GAP-DCI; Includes publicly available documents filed from Jan. 6, 2021-Feb. 3, 2021; (96 pages).
Documents filed with U.S. District Court Proceedings for *D3D Technologies, Inc.* v. *Microsoft Corporation*; U.S. District Court, Middle District of Florida Orlando Division; Civil Action No. 6:20-cv-01699-GAP-DCI; Includes publicly available documents filed from Feb. 4, 2021-Apr. 6, 2021; (1,242 pages).
Documents filed with U.S. District Court Proceedings for *D3D Technologies, Inc.* v. *Microsoft Corporation*; U.S. District Court, Middle District of Florida Orlando Division; Civil Action No. 6:20-cv-01699-GAP-DCI; Includes publicly available documents filed on Apr. 19. 2021; (76 pages).
Documents filed with U.S. District Court Proceedings for *D3D Technologies, Inc.* v. *Microsoft Corporation*; U.S. District Court, Middle District of Florida Orlando Division; Civil Action No. 6:20-cv-01699-GAP-DCI; Includes publicly available documents filed from Apr. 27, 2021-Jun. 11, 2021; (182 pages).
Defendant Microsoft Corporation's Preliminary Noninfringement Contentions for *D3D Technologies, Inc.* v. *Microsoft Corporation*; U.S. District Court, Middle District of Florida Orlando Division; Civil Action No. 6:20-cv-01699-GAP-DCI; Filed Feb. 4, 2021 (1,114 Pages).
Defendant Microsoft Corporation's Supplemental Invalidity Contentions for *D3D Technologies, Inc.* v. *Microsoft Corporation*; U.S. District Court, Middle District of Florida Orlando Division; Civil Action No. 6:20-cv-01699-GAP-DCI; Filed Apr. 19, 2021 (143 Pages).
Petition for Inter Partes Review of U.S. Pat. No. 8,384,771, including Exhibits 1001-1012 and 1020-1022; Case No. IPR2021-00647, filed Mar. 23, 2021 (808 pages).
Documents filed with *Microsoft Corporation* v. *D3D Technologies, Inc.*; United States Patent and Trademark Office—Before the Patent Trial and Appeal Board, Case No. IPR2021-00647; Filed on Mar. 26, 2021 (5 pages).

(56) References Cited

OTHER PUBLICATIONS

Documents filed with *Microsoft Corporation v. D3D Technologies, Inc.*; United States Patent and Trademark Office—Before the Patent Trial and Appeal Board, Case No. IPR2021-00647; Filed on Apr. 15, 2021 (8 pages).
Petition for Inter Partes Review of U.S. Pat. No. 9,349,183, including Exhibits 1001-1007, 1009; 1010; 1013; 1014, and 1020-1022; Case No. IPR2021-00648, filed Mar. 23, 2021 (1,020 pages).
Documents filed with *Microsoft Corporation v. D3D Technologies, Inc.*; United States Patent and Trademark Office—Before the Patent Trial and Appeal Board, Case No. IPR2021-00648; Filed on Mar. 26, 2021 (5 pages).
Documents filed with *Microsoft Corporation v. D3D Technologies, Inc.*; United States Patent and Trademark Office—Before the Patent Trial and Appeal Board, Case No. IPR2021-80648; Filed on Apr. 15, 2021 (8 pages).
Petition for Inter Partes Review of U.S. Pat. No. 9,473,766, including Exhibits 1001-1024; Case No. IPR2021-00703, filed Apr. 7, 2021 (1,441 pages).
Documents filed with *Microsoft Corporation v. D3D Technologies, Inc.*; United States Patent and Trademark Office—Before the Patent Trial and Appeal Board, Case No. IPR2021-00703; Filed on Apr. 15, 2021 (14 pages).
Petition for Inter Partes Review of U.S. Pat. No. 9,980,691, including Exhibits 1001-1012: 1015-1016; and 1019-1029; Case No. IPR2021-00877, filed May 21, 2021 (1,087 pages).
Documents fifed with *Microsoft Corporation v. D3D Technologies, Inc.*; United States Patent and Trademark Office—Before the Patent Trial and Appeal Board, Case No. IPR2021-00877; Filed on Jun. 8, 2021 (5 pages).
Petition for Inter Partes Review of U.S. Pat. No. 9,980,691, including Exhibits 1001-1004 and 1006-1029; Case No. IPR2021-00878, filed May 21, 2021 (1,213 pages).
Documents filed with *Microsoft Corporation v. D3D Technologies, Inc.*; United States Patent and Trademark Office—Before the Patent Trial and Appeal Board, Case No. IPR2021-00878; Filed on Jun. 8, 2021 (5 pages).
Documents filed with U.S. District Court Proceedings for *D3D Technologies*, Inc. v. *Microsoft Corporation*; U.S. District Court, Middle District of Florida Orlando Division; Civil Action No. 6:20-cv-01699-GAP-DCI; Includes publicly available documents filed from Jun. 16, 2021-Oct. 1, 2021; (139 pages).
Patent Owner's Preliminary Response, including Exhibits 2001-2005 filed with *Microsoft Corporation v. D3D Technologies, Inc.*; United States Patent and Trademark Office—Before the Patent Trial and Appeal Board, Case No. IPR2021-00647; Filed on Jun. 25, 2021 (120 pages).
Documents filed with *Microsoft Corporation v. D3D Technologies, Inc.*; United States Patent and Trademark Office—Before the Patent Trial and Appeal Board, Case No. IPR2021-00647; Filed on Jul. 15, 2021 (3 pages).
Petitioner's Reply to Patent Owner's Preliminary Response, including Exhibits 1025-1032 filed with *Microsoft Corporation v. D3D Technologies, Inc.*; United States Patent and Trademark Office—Before the Patent Trial and Appeal Board, Case No. IPR2021-00647; Filed on Jul. 22, 2021 (133 pages).
Patent Owner's Sur-Reply to Petitioner's Reply to Patent Owner's Preliminary Response, including Exhibits 2007-2016 filed with *Microsoft Corporation v. D3D Technologies, Inc.*; United States Patent and Trademark Office—Before the Patent Trial and Appeal Board, Case No. IPR2021-00647; Filed on Jul. 26, 2021 (39 pages).
Decision Granting Institution of Inter Partes Review, including Exhibit 300 and Scheduling Order filed with *Microsoft Corporation v. D3D Technologies, Inc.*; United States Patent and Trademark Office—Before the Patent Trial and Appeal Board, Case No. IPR2021-00647; Filed on Sep. 1, 2021 (46 pages).
Patent Owner's Preliminary Response, including Exhibits 2001-2005, filed with *Microsoft Corporation v. D3D Technologies, Inc.*; United States Patent and Trademark Office—Before the Patent Trial and Appeal Board, Case No. IPR2021-00648; Filed on Jun. 25, 2021 (125 pages).
Documents filed with *Microsoft Corporation v. D3D Technologies, Inc.*; United States Patent and Trademark Office—Before the Patent Trial and Appeal Board, Case No. IPR2021-00648; Filed on Jul. 23, 2021 (3 pages).
Petitioner's Reply to Patent Owner's Preliminary Response, including Exhibits 1025-1032 filed with *Microsoft Corporation v. D3D Technologies, Inc.*; United States Patent and Trademark Office—Before the Patent Trial and Appeal Board, Case No. IPR2021-00648; Filed on Jul. 30, 2021 (133 pages).
Patent Owner's Sur-Reply to Petitioner's Reply to Patent Owner's Preliminary Response, including Exhibits 2007-2016 filed with *Microsoft Corporation v. D3D Technologies, Inc.*; United States Patent and Trademark Office—Before the Patent Trial and Appeal Board, Case No. IPR2021-00648; Filed on Aug. 2, 2021 (39 pages).
Decision Granting Institution of Inter Partes Review and Scheduling Order filed with *Microsoft Corporation v. D3D Technologies, Inc.*; United States Patent and Trademark Office—Before the Patent Trial and Appeal Board, Case No. IPR2021-00648; Filed on Sep. 1, 2021 (72 pages).
Patent Owner's Preliminary Response, including Exhibits 2001-2004 filed with *Microsoft Corporation v. D3D Technologies, Inc.*; United States Patent and Trademark Office—Before the Patent Trial and Appeal Board, Case No. IPR2021-00703; Filed on Jul. 14, 2021 (82 pages).
Documents filed with *Microsoft Corporation v. D3D Technologies, Inc.*; United States Patent and Trademark Office—Before the Patent Trial and Appeal Board. Case No. IPR2021-00703; Filed on Jul. 15, 2021 (3 pages).
Petitioner's Reply to Patent Owner's Preliminary Response including Exhibits 1025-1032 filed with *Microsoft Corporation v. D3D Technologies, Inc.*; United States Patent and Trademark Office—Before the Patent Trial and Appeal Board, Case No. IPR2021-00703; Filed on Jul. 22, 2021 (134 pages).
Patent Owner's Sur-Reply to Petitioner's Reply to Patent Owner's Preliminary Response including Exhibits 2007-2016 filed with *Microsoft Corporation v. D3D Technologies, Inc.*; United States Patent and Trademark Office—Before the Patent Trial and Appeal Board, Case No. IPR2021-00703; Filed on Jul. 26, 2021 (39 pages).
Documents filed with *Microsoft Corporation v. D3D Technologies, Inc.*; United States Patent and Trademark Office—Before the Patent Trial and Appeal Board, Case No. IPR2021-00877; Filed on Sep. 1, 2021 (15 pages).
Patent Owner's Preliminary Response, Including Exhibits 2001 and 2003-2018, filed with *Microsoft Corporation v. D3D Technologies, Inc.*; United States Patent and Trademark Office—Before the Patent Trial and Appeal Board, Case No. IPR2021-88877; Filed on Sep. 8, 2021 (293 pages).
Documents filed with *Microsoft Corporation v. D3D Technologies, Inc.*; United States Patent and Trademark Office—Before the Patent Trial and Appeal Board, Case No. IPR2021-00877; Filed Between Sep. 8, 2021-Sep. 13, 2021 (12 pages).
Petitioner's Reply to Patent Owner's Preliminary Response, including Exhibits 1031-1042, filed with *Microsoft Corporation v. D3D Technologies, Inc.*; United States Patent and Trademark Office—Before the Patent Trial and Appeal Board, Case No. IPR2021-00877; Filed on Sep. 20, 2021 (248 pages).
Patent Owner's Sur-Reply to Petitioner's Reply to Patent Owner's Preliminary Response filed with *Microsoft Corporation v. D3D Technologies, Inc.*; United States Patent and Trademark Office—Before the Patent Trial and Appeal Board, Case No. IPR2021-00877; Filed on Sep. 22, 2021 (10 pages).
Documents filed with *Microsoft Corporation v. D3D Technologies, Inc.*; United States Patent and Trademark Office—Before the Patent Trial and Appeal Board, Case No. IPR2021-00878; Filed on Sep. 1, 2021 (15 pages).
Patent Owner's Preliminary Response, Including Exhibits, 2001 and 2003-2018 filed with *Microsoft Corporation v. D3D Technologies, Inc.*; United States Patent and Trademark Office—Before the Patent Trial and Appeal Board, Case No. IPR2021-00878; Filed on Sep. 8, 2021 (267 pages).

(56) References Cited

OTHER PUBLICATIONS

Documents filed with *Microsoft Corporation v. D3D Technologies, Inc.*; United States Patent and Trademark Office—Before the Patent Trial and Appeal Board, Case No. IPR2021-88878; Filed between Sep. 8, 2021—Sep. 13, 2021 (12 pages).

Petitioner's Reply to Patent Owner's Preliminary Response, Including Exhibits, 1031-1042 filed with *Microsoft Corporation v. D3D Technologies, Inc.*: United States Patent and Trademark Office—Before the Patent Trial and Appeal Board, Case No. IPR2021-00878; Filed on Sep. 20, 2021 (248 pages).

Patent Owner's Sur-Reply to Petitioner's Reply to Patent Owner's Preliminary Response filed with *Microsoft Corporation v. D3D Technologies, Inc.*; United States Patent and Trademark Office—Before the Patent Trial and Appeal Board, Case No. IPR2021-00878; Filed on Sep. 22, 2021 (10 pages).

Claim Construction Order in U.S. District Court Proceedings for *D3D Technologies, Inc. v. Microsoft Corporation*; U.S. District Court, Middle District of Florida Orlando Division; Civil Action No. 6:20-cv-01699-PGB-DCI; Entered Dec. 3, 2021; Documents No. 126; (17 pages).

IPR2021-00647 Documents in *Microsoft Corporation v. D3D Technologies, Inc.* Including Patent Owner Response, Petitioner's Reply, and Patent Owner Sur-Reply; United States Patent and Trademark Office—Before the Patent Trial and Appeal Board, Case No. IPR2021-00647; Entered Nov. 21, 2021-Apr. 22, 2022 (557 pages).

IPR2021-00647 Exhibit Lists and Demonstratives in *Microsoft Corporation v. D3D Technologies, Inc.* United States Patent and Trademark Office—Before the Patent Trial and Appeal Board, Case No. IPR2021-00647; Entered Jul. 25, 2022 (65 pages).

IPR2021-00647 Final Written Decision in *Microsoft Corporation v. D3D Technologies, Inc.*; United States Patent and Trademark Office—Before the Patent Trial and Appeal Board, Case No. IPR2021-00647; Entered on Aug. 3, 2022 (31 pages).

IPR2021-00647 Hearing Transcript in *Microsoft Corporation v. D3D Technologies, Inc.*; United States Patent and Trademark Office—Before the Patent Trial and Appeal Board, Case No. IPR2021-00647; Entered Jul. 6, 2022 (91 pages).

IPR2021-00648 Documents in *Microsoft Corporation v. D3D Technologies, Inc.* Including Patent Owner Response; United States Patent and Trademark Office—Before the Patent Trial and Appeal Board, Case No. IPR2021-00648; Entered Nov. 24, 2021-Feb. 15, 2022 (255 pages).

IPR2021-00648 Exhibit Lists and Demonstratives in *Microsoft Corporation v. D3D Technologies, Inc.* United States Patent and Trademark Office—Before the Patent Trial and Appeal Board, Case No. IPR2021-00648; Entered May 25, 2022, (63 pages).

IPR2021-00648 Final Written Decision in *Microsoft Corporation v. D3D Technologies, Inc.*; United States Patent and Trademark Office—Before the Patent Trial and Appeal Board, Case No. IPR2021-00648; Entered Aug. 22, 2022 (138 pages).

IPR2021-00648 Hearing Transcript in *Microsoft Corporation v. D3D Technologies, Inc.*; United States Patent and Trademark Office—Before the Patent Trial and Appeal Board, Case No. IPR2021-00648; Entered Jul. 6, 2022 (91 pages).

IPR2021-00703 Documents in *Microsoft Corporation v. D3D Technologies, Inc.* Including Patent Owner Response and Petitioner's Reply; United States Patent and Trademark Office—Before the Patent Trial and Appeal Soard, Case No. IPR2021-00703; Entered Dec. 29, 2021-Jun. 29, 2022 (141 pages).

IPR2021-00703 Exhibit List and Demonstratives in *Microsoft Corporation v. D3D Technologies, Inc.* United States Patent and Trademark Office—Before the Patent Trial and Appeal Board, Case No. IPR2021-00703; Entered Jul. 6-8, 2022 (52 pages).

IPR2021-00703 Hearing Transcript in *Microsoft Corporation v. D3D Technologies, Inc.*; United States Patent and Trademark Office—Before the Patent Trial and Appeal Board, Case No. IPR2021-00703; Entered Aug. 15, 2022 (39 pages).

IPR2021-00703 Institution Decision in *Microsoft Corporation v. D3D Technologies, Inc.*; United States Patent and Trademark Office—Before the Patent Trial and Appeal Board, Case No. IPR2021-00703; Entered Oct. 12, 2021 (86 pages).

IPR2021-00877 Non-Institution Decision in *Microsoft Corporation v. D3D Technologies, Inc.*; United States Patent and Trademark Office—Before the Patent Trial and Appeal Board, Case No. IPR2021-00877; Entered Dec. 2, 2021 (45 pages).

IPR2021-00878 Documents in *Microsoft Corporation v. D3D Technologies, Inc.* Including Patent Owner Response, Petitioner's Reply, and Patent Owner Sur-Reply; United States Patent and Trademark Office—Before the Patent Trial and Appeal Board, Case No. IPR2021-00878; Entered Dec. 16, 2021-Jul. 21, 2022 (542 pages).

IPR2021-00878 Institution Decision in *Microsoft Corporation v. D3D Technologies, Inc.*; United States Patent and Trademark Office—Before the Patent Trial and Appeal Board, Case No. IPR2021-00878; Entered Dec. 2, 2021 (67 pages).

IPR2021-00878 Pre-lnstitution Decision Documents in *Microsoft Corporation v. D3D Technologies, Inc.* United States Patent and Trademark Office—Before the Patent Trial and Appeal Board, Case No. IPR2021-00878; Entered Nov. 30, 2021 (27 pages).

IPR2021-01325 Fuchs Declaration in Support of Petition in *Microsoft Corporation v. D3D Technologies, Inc.*; United States Patent and Trademark Office—Before the Patent Trial and Appeal Board, Case No. PR2021-01325; Entered Aug. 25, 2021 (123 pages).

IPR2021-01325 Institution Decision in *Microsoft Corporation v. D3D Technologies, Inc.*; United States Patent and Trademark Office—Before the Patent Trial and Appeal Board, Case No. IPR2021-01325; Entered Feb. 18, 2022 (72 pages).

IPR2021-01325 Petition in *Microsoft Corporation v. D3D Technologies, Inc.*; United States Patent and Trademark Office—Before the Patent Trial and Appeal Board, Case No. IPR2021-01325; Entered Aug. 25, 2021 (120 pages).

IPR2021-01325 Post-Institution Docs in *Microsoft Corporation v. D3D Technologies, Inc.* including Patent Owner Response; United States Patent and Trademark Office—Before the Patent Trial and Appeal Board, Case No. IPR2021-01325; Entered Apr. 14, 2021-Jun. 21, 2022 (62 pages).

IPR2021-01325 Pre-lnstitution Documents in *Microsoft Corporation v. D3D Technologies, Inc.* Including Patent Owner Preliminary Response, Petitioner's Preliminary Reply, and Patent Owner Preliminary Sur-Reply; United States Patent and Trademark Office—Before the Patent Trial and Appeal Board, Case No. IPR2021-01325; Entered Sep. 13, 2021-Feb. 3, 2022 (172 pages).

IPR2021-00878 Documents filed with *Microsoft Corporation v. D3D Technologies, Inc.*; United States Patent and Trademark Office—Before the Patent Trial and Appeal Board, Case No. PR2021-00878; Filed between Sep. 23-Oct. 7, 2022 (91 pages).

IPR2021-00703 Final Written Decision in *Microsoft Corporation v. D3D Technologies, Inc.*; United States Patent and Trademark Office—Before the Patent Trial and Appeal Board, Case No. IPR2021-00703; Entered on Oct. 6, 2022 (77 pages).

* cited by examiner

Initial scan — Follow up scan

Initial scan — Follow up scan

Initial scan — Follow up scan

INTERACTIVE 3D CURSOR FOR USE IN MEDICAL IMAGING

CROSS REFERENCE TO RELATED APPLICATIONS

This application is a Continuation of U.S. patent application Ser. No. 17/122,518, filed Dec. 15, 2020, now U.S. Pat. No. 11,036,311, which is a Continuation of Ser. No. 17/021,548, filed Sep. 15, 2020, now U.S. Pat. No. 10,936,090, which is a Continuation of U.S. patent application Ser. No. 15/878,463, filed Jan. 24, 2018, now U.S. Pat. No. 10,795,457, which is a Continuation-in-Part of U.S. patent application Ser. No. 14/877,442, filed Oct. 7, 2015, now U.S. Pat. No. 9,980,691, which is a Continuation-in-Part of U.S. patent application Ser. No. 12/176,569, filed Jul. 21, 2008, now U.S. Pat. No. 9,349,183, which is a Continuation-in-Part of U.S. patent application Ser. No. 11/941,578, filed Nov. 16, 2007, now U.S. Pat. No. 8,384,771, which claims the benefit of and priority under 35 U.S.C. § 119(e) to U.S. Patent Application No. 60/877,931, filed Dec. 28, 2006, each of which are incorporated herein by reference in their entirety.

TECHNICAL FIELD

Aspects of this disclosure are generally related to human-machine interfaces, and more particularly to cursors.

BACKGROUND

The typical arrow-shaped cursor presented by a computer operating system is zero-dimensional. A zero-dimensional cursor designates the location of a single point in a space such as a two-dimensional window presented on a monitor. Mouse buttons can be used in combination with movement of the cursor to select objects in the two-dimensional space, but at any given instant of time a zero-dimensional cursor position designates only a single point in space.

The current standard for diagnostic radiologists reviewing computed tomography (CT) or magnetic resonance imaging (MRI) studies is a slice-by-slice method. A conventional keyboard, monitor, and mouse with a zero-dimensional cursor are used for manipulating the images. The use of mouse buttons and cursor movement for manipulating the images can become burdensome. For example, many images are included in radiology studies that are performed for the follow up of cancer to determine the response to treatment. The ability to recognize and analyze differences between images can be important. As an example, the recent Investigation of Serial Studies to Predict Your Therapeutic Response with Imaging and Molecular Analysis (I-SPY) trial tracked the changes in the tumor over multiple magnetic resonance imaging (MRI) scans during the administration of neoadjuvant chemotherapy (NACT). It has been noted that the phenotypic appearance (e.g., shape, margins) of a tumor correlated with the pathologic response to NACT. A more efficient and accurate interface for manipulating and presenting medical images would therefore have utility.

Known techniques for 3D viewing of medical images are described in U.S. Pat. No. 9,349,183, Method and Apparatus for Three Dimensional Viewing of Images, issued to Douglas, U.S. Pat. No. 8,384,771, Method and Apparatus for Three Dimensional Viewing of Images, issued to Douglas, Douglas, D. B., Petricoin, E. F., Liotta L., Wilson, E. D3D augmented reality imaging system: proof of concept in mammography. Med Devices (Auckl), 2016; 9:277-83, Douglas, D. B., Boone, J. M., Petricoin, E., Liotta, L., Wilson, E. Augmented Reality Imaging System: 3D Viewing of a Breast Cancer. J Nat Sci. 2016; 2(9), and Douglas, D. B., Wilke, C. A., Gibson, J. D., Boone, J. M., Wintermark, M. Augmented Reality: Advances in Diagnostic Imaging. Multimodal Technologies and Interaction, 2017; 1(4):29. In D3D imaging, the radiologist wears an augmented reality (AR), mixed reality (MR) or virtual reality (VR) headset and uses a joystick or gaming controller. Advantages include improved depth perception and human machine interface. Still, there are several challenges faced with this approach. First, an area of interest (e.g. tumor) may be in close proximity to structures that are similar in composition/density. Isolating the area of interest for better examination may be difficult. Second, many soft tissues in the body are mobile and deformable, so it can be difficult to achieve the best orientation to properly compare the tumor at multiple time points. Efficiently aligning the orientation to do so may be difficult. Third, certain portions of a tumor can respond to treatment and decrease in size while other portions of a tumor demonstrate increases in size. The pattern of tumor shrinkage has important prognostic implications. Furthermore, composition and complex morphologic features including spiculations (spikes extending from the surface), irregular margins and enhancement also have important implications. Consequently, there is a need for a system that facilitates recognition of the subtle, yet important changes in size, shape and margins. Fourth, a patient with metastatic cancer has several areas of interest in different areas of the body. It is difficult and time consuming to find each of the areas of interest at every time point to determine interval change. Consequently, there is a need for a system that enables the observer to do this efficiently.

SUMMARY

All examples, aspects and features mentioned in this document can be combined in any technically possible way.

In accordance with an aspect of the invention a method comprises: generating a three-dimensional cursor that has a non-zero volume; responsive to a first input, moving the three-dimensional cursor within a three-dimensional image; responsive to a second input, selecting a volume of the three-dimensional image designated by the three-dimensional cursor; and responsive to a third input, presenting a modified version of the selected volume of the three-dimensional image. In some implementations presenting the modified version of the selected volume of the three-dimensional image comprises removing an un-selected volume of the three-dimensional image from view. In some implementations presenting the modified version of the selected volume of the three-dimensional image comprises changing transparency of presented tissues within the selected volume. In some implementations presenting the modified version of the selected volume of the three-dimensional image comprises filtering a selected tissue to remove the selected tissue from view. In some implementations presenting the three-dimensional cursor with measurement markings on at least one edge, surface or side. In some implementations presenting the modified version of the selected volume of the three-dimensional image comprises presenting inputted location indicators. In some implementations presenting the modified version of the selected volume of the three-dimensional image comprises presenting inputted annotations. Some implementations comprise changing a size dimension of the three-dimensional cursor responsive to a fourth input. Some implementations comprise changing a geometric shape of the three-dimensional cursor responsive to a fifth input. Some implementations comprise automatically generating a statistical representation of the selected volume of the three-dimensional image. In some implementations presenting the modified version of the selected volume of the three-dimensional image comprises presenting at least one tissue type with false color. In some implementations presenting the modified version of the selected volume of the three-dimensional image comprises presenting volumetric changes over time with false color. Some implementations comprise presenting multiple computed tomography images associated with the selected volume using reference lines. Some implementations comprise presenting multiple axial computed tomography images associated with the selected volume using reference lines. Some implementations comprise presenting a maximum intensity projection (MIP) image of a positron emission tomography (PET) scan with the three-dimensional cursor overlaid thereon to indicate orientation and location of the selected volume. Some implementations comprise presenting a radiology report enhanced with information obtained using the three-dimensional cursor. Some implementations comprise automatically calculating and presenting a quantitative analysis and a qualitative analysis associated with multiple time points. Some implementations comprise presenting the modified version of the selected volume of the three-dimensional image comprises presenting inputted registration markers. Some implementations comprise automatically calculating volumetric change based on the registration markers. Some implementations comprise automatically re-orienting the selected volume of the three-dimensional image based on the registration markers. Some implementations comprise using multiple volumes selected with the three-dimensional cursor to designate a pre-operative planning pathway for guiding surgical intervention. Some implementations comprise presenting the selected volume with an augmented reality, virtual reality or mixed reality headset.

In accordance with an aspect of the invention an apparatus comprises: a computing device; and a human-machine interface comprising a three-dimensional cursor that has a non-zero volume; the human-machine interface moving the three-dimensional cursor within a three-dimensional image responsive to a first input; the human-machine interface selecting a volume of the three-dimensional image designated by the three-dimensional cursor responsive to a second input; and the human-machine interface presenting a modified version of the selected volume of the three-dimensional image responsive to a third input. In some implementations, the human-machine interface removes an un-selected volume of the three-dimensional image from view. In some implementations, the human-machine interface changes transparency of presented tissues within the selected volume. In some implementations, the human-machine interface filters a selected tissue to remove the selected tissue from view. In some implementations, the human-machine interface presents the three-dimensional cursor with measurement markings on at least one edge, surface or side. In some implementations, the human-machine interface receives and implements inputted location indicators. In some implementations, the human-machine interface receives and implements inputted annotations. In some implementations, the human-machine interface changes a size dimension of the three-dimensional cursor responsive to a fourth input. In some implementations, the human-machine interface changes a geometric shape of the three-dimensional cursor responsive to a fifth input. In some implementations, the human-machine interface automatically generates and presents a statistical representation of the selected volume of the three-dimensional image. In some implementations, the human-machine interface presents at least one tissue type with false color. In some implementations, the human-machine interface presents volumetric changes over time with false color. In some implementations, the human-machine interface presents multiple computed tomography images associated with the selected volume using reference lines. In some implementations, the human-machine interface presents multiple axial computed tomography images associated with the selected volume using reference lines. In some implementations, the human-machine interface presents a maximum intensity projection (MIP) image of a positron emission tomography (PET) scan with the three-dimensional cursor overlaid thereon to indicate orientation and location of the selected volume. In some implementations, the human-machine interface presents a radiology report enhanced with information obtained using the three-dimensional cursor. In some implementations, the human-machine interface automatically calculates and presents a quantitative analysis and a qualitative analysis associated with multiple time points. In some implementations, the human-machine interface presents inputted registration markers. In some implementations, the human-machine interface automatically calculates volumetric change after appropriate registration using the registration markers. In some implementations, the human-machine interface automatically re-orients the selected volume of the three-dimensional image based on the registration markers. In some implementations, the human-machine interface presents multiple volumes selected with the three-dimensional cursor to designate a pre-operative planning pathway for guiding surgical intervention. In some implementations, the human-machine interface presents the selected volume with an augmented reality, virtual reality or mixed reality headset.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Some aspects, features and implementations described herein may include machines such as computers, electronic components, radiological components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1A:
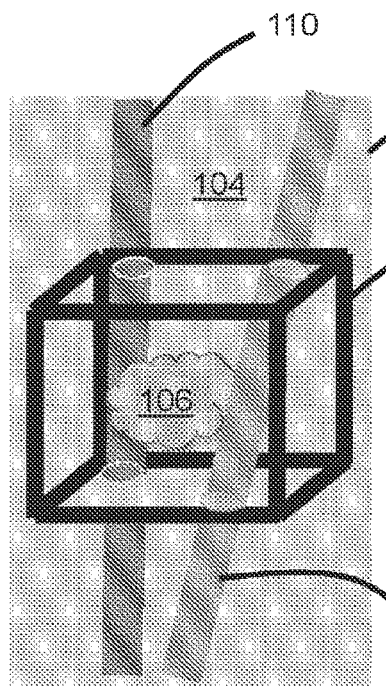
FIG. 1A illustrates a 3D cursor selecting a volume of interest from a three-dimensional medical image.

FIG. 1A illustrates a 3D (three-dimensional) cursor 100 overlaid on a three-dimensional medical image 102. In the illustrated example, the 3D cursor 100 defines a cubic volume of interest. The medical image 102 could include any portion of a body, or an entire body, for example and without limitation. For purposes of explanation the medical image 102 includes different types of tissue. More specifically, the image includes a background material 104, such as fat, a lobulated mass 106, a tubular-shaped vein 108, and an artery 110. The 3D cursor 100 can be moved relative to the image, e.g. in three dimensions, such as by manipulating an IO device such as a 3D mouse, for example and without limitation. A button click or other input designates (selects) the portion of the image that is located inside the three-dimensional volume of the 3D cursor 100. Distinguishing between a 3D image portion selected by a 3D cursor and other unselected image portions is described in US 2016/0026266 and U.S. Pat. No. 8,384,771, both of which are incorporated by reference.

Figure 1B:
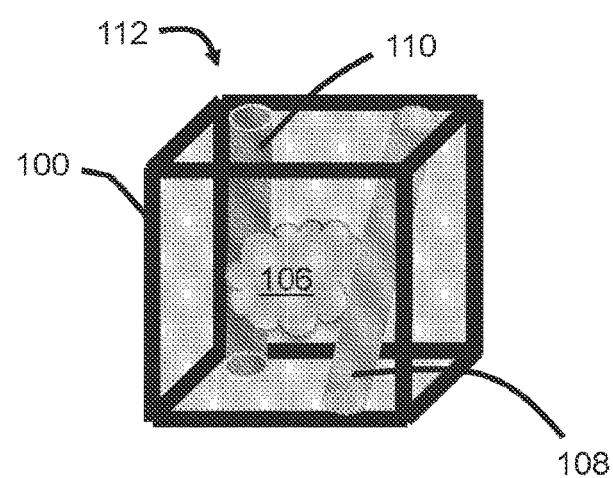
FIG. 1B illustrates the volume of interest selected with the 3D cursor; unselected portions have been removed from view.

FIG. 1B illustrates the selected image portion of FIG. 1A. More particularly, unselected portions of the image located outside of an image portion 112 selected with the 3D cursor 100 have been filtered-out or otherwise completely removed from view. Consequently, the removed portions of the image do not obstruct or hinder the view of the selected image portion. Moreover, the selected image portion 112 can be manipulated and viewed as a separate and distinct image from the larger medical image 102 from which it was selected.

Figure 1C:
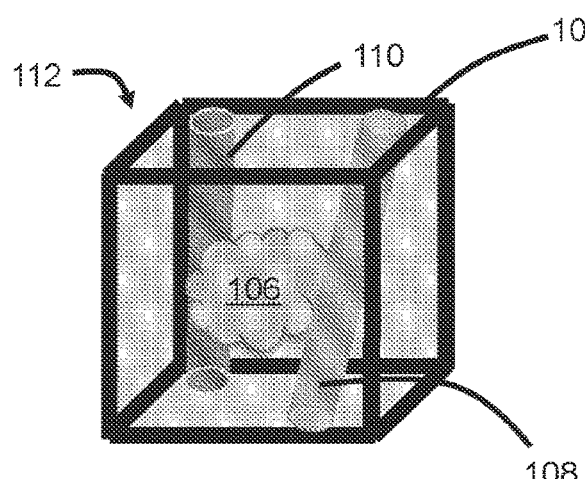
FIG. 1C illustrates modification of the transparency of the selected volume of interest.

FIG. 1C illustrates modification of the transparency of the selected image portion 112. More specifically, transparency may be decreased and/or increased such that tissues and other features can be better observed, e.g. such that overlapping tissues and features are visible. For example, tissues and features located proximate to the back of the selected image portion such as lobulated mass 106 can be seen through overlapping tissues and features located proximate to the front of the selected image portion such as vein 108, when transparency is sufficiently increased. The transparency may be manipulated with the IO device to achieve various levels of transparency. Further, different levels of transparency may be applied to different portions of the selected image portion.

Figure 1D:
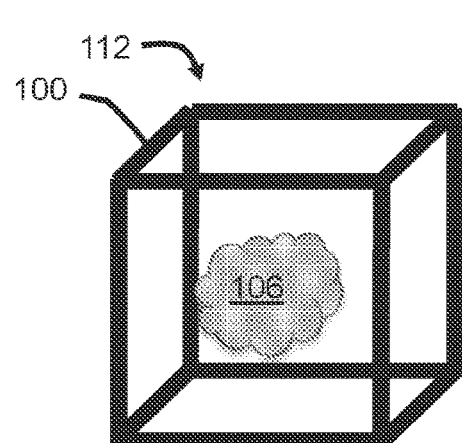
FIG. 1D illustrates filtering of selected areas of the selected volume of interest.

FIG. 1D illustrates filtering of selected areas or tissues of the selected image portion 112 to remove those areas or tissues from view. In the illustrated example the background material 104, vein 108, and an artery 110 have been removed from view, leaving only the lobulated mass 106. The tissues to be filtered (removed from view) may be selected based on geometric shape, color, brightness, density, and any other of a variety of available image data, either alone or in combination. Moreover, a designated volume defined by a geometric shape may be removed, e.g. a geometric shape that traverses tissue boundaries.

Transparency modification and tissue filtering facilitate presentation of certain tissue types of concern, both within the cursor and outside of the cursor. Currently, the medical professional must see through any tissue within the cursor but external to the tissue type of concern from the viewing point of the medical professional, thus degrading the visibility of the tissue of concern. The illustrated improvements enable the medical professional to change the transparency of any tissue within the cursor-defined volume but external to the tissue type of concern. Alternatively, tissue types not of concern are subtracted from the volume contained within the interactive 3D cursor, leaving only the tissue of concern in the presented image. Multiple interactive 3D cursors in combination can be used to obtain varying patterns of tissue subtraction. This helps to overcome the limitations of degraded visibility due to tissue within the cursor but external to the tissue type of concern from the viewing point of the medical professional.

Figure 2:
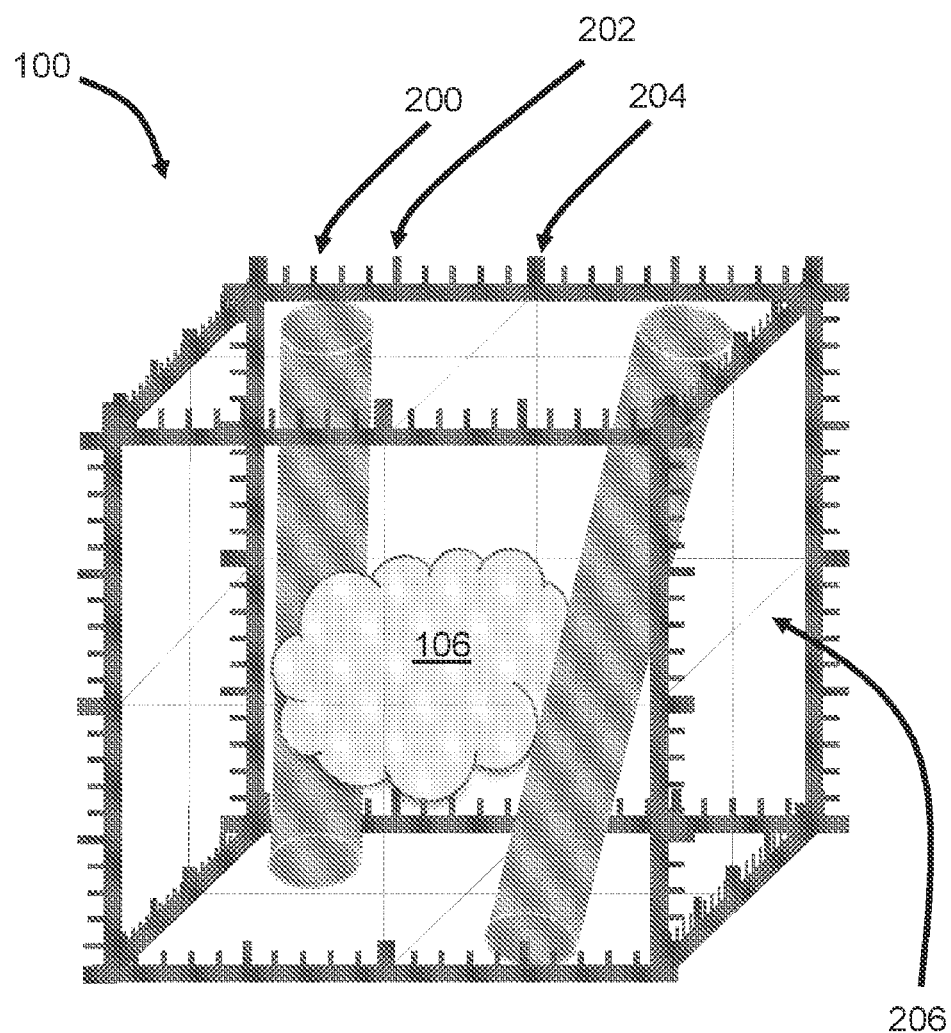
FIG. 2 illustrates a variant of the 3D cursor of FIG. 1A with measurement markings on edges and sides.

FIG. 2 illustrates an implementation of the 3D cursor 100 with dimensional measurement markings. Dimensional measurement markings may be available as a feature that can be turned ON and OFF. In the illustrated example, the 3D cursor is a 2 cm by 2 cm by 2 cm cube. The dimensional measurement markings include tick marks 200, 202, and 204 that respectively designate 1 mm, 5 mm, and 1 cm increments along the edges of the cube (and thus representing three dimensions). Tick marks that represent different magnitudes may be uniquely represented to facilitate visual size determination of the lobulated mass 106 that represents the lesion of interest. 1 cm markings 206 are presented in each of two dimensions on each side of the cube.

The dimensional measurement markings can help serve as a reference for radiologist's activities to include visual assessment, orientation, comparisons with prior scans or measurements. Advantages may include mitigating the current lack of metrics are available to the medical professional to understand the size of the cursor and/or of the tissue elements contained within the cursor. This implementation places measurement metrics on each edge and side of the cursor to help enable the medical professional to rapidly understand the size of the subtended volume within the cursor. In the case where the cursor encapsulates a volume of concern such as a tumor, the three-dimensional size could be recorded in the medical professional report. This can help the visual assessment of each portion of the tumor to aid in the assessment of small changes in size of findings including lobulations of a mass's margin and spiculations.

Figure 3:
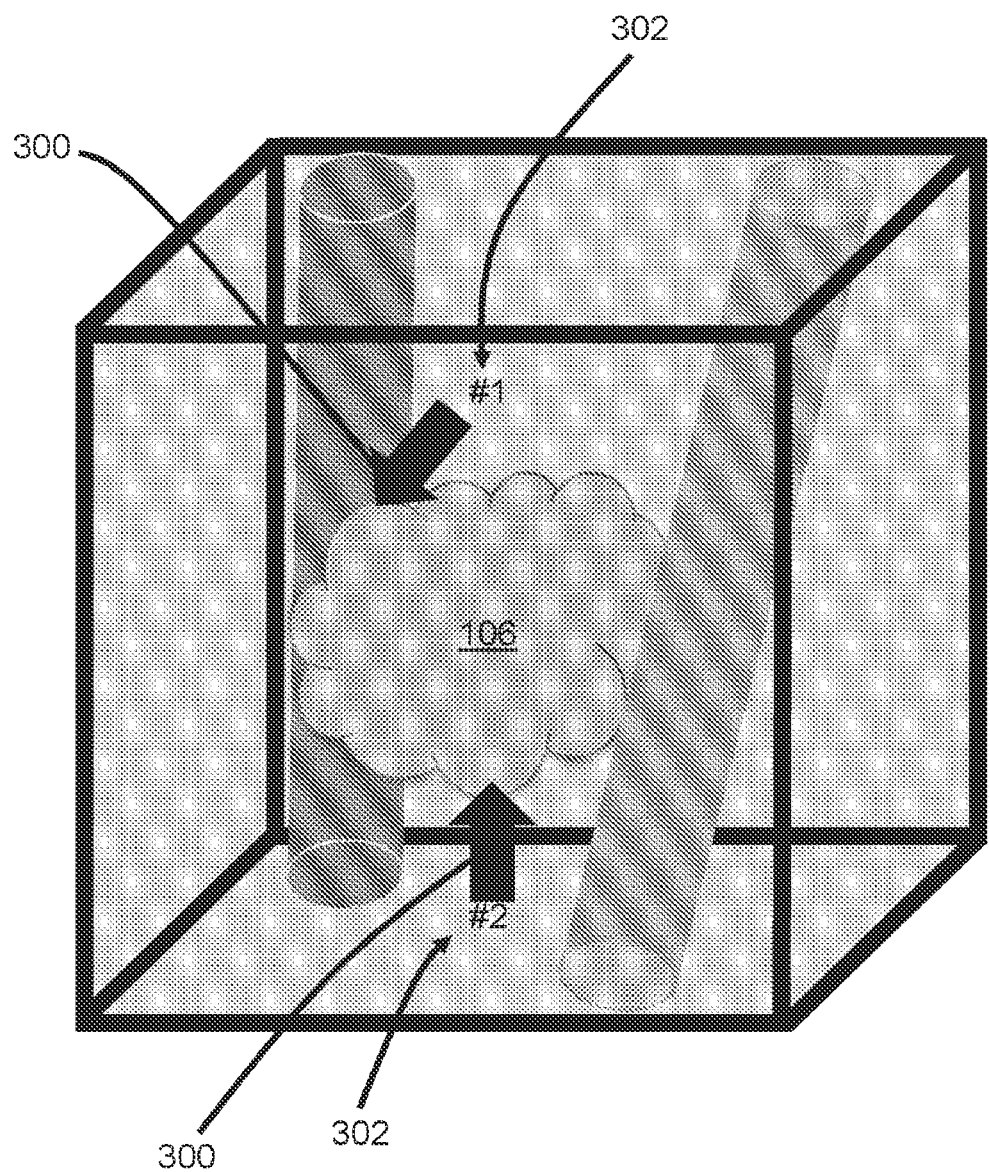
FIG. 3 illustrates location indicators and annotations positioned relative to the portion of the image within the selected volume of interest.

Referring to FIG. 3, location indicators 300 and annotations 302 may be placed by the radiologist or by automated techniques to highlight locations or regions of concern within the interactive 3D cursor. The location indicators may specify a point or region within the volume of the 3D cursor. Annotations can be added manually by the radiologist or by automated techniques to describe areas that are of concern, e.g., growing, spiculation, irregular margin, indistinct margin, etc. If spiculations are on the surface of a tumor, this could be an indicator of potential malignancy. The location indicators, such as, but not limited to, arrow(s) pointing to key regions of interest within/outside the 3D cursor helps to overcome the limitation of the inability to mark key points within the cursor. This feature will be useful in discussions between medical professions regarding a patient's condition. It will also be useful in communicating imaging findings between a medical professional and a patient.

Figure 4A:
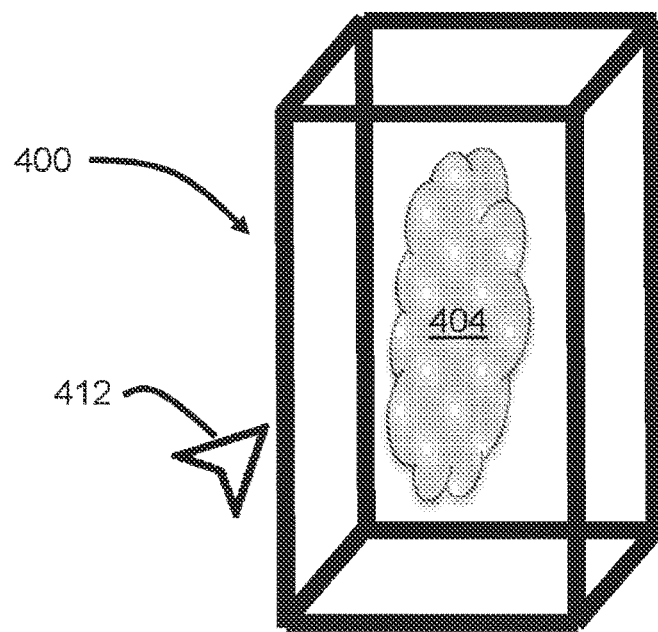
FIGS. 4A, 4B, and 4C illustrate three different examples of geometric shapes of the 3D cursor of FIG. 1A.
Figure 4B:
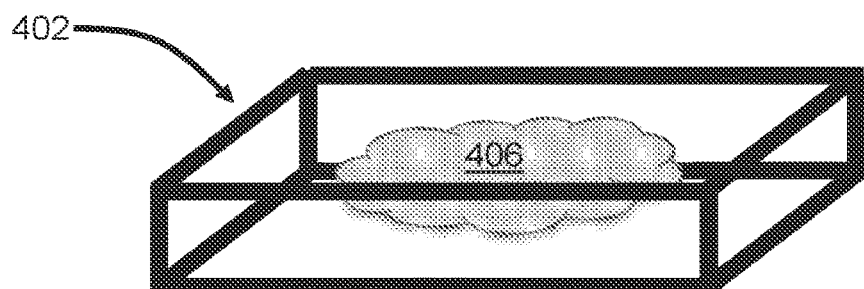
Figure 4C:
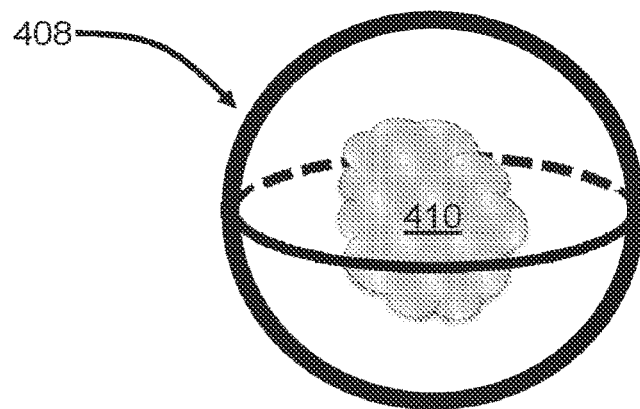

Referring to FIGS. 4A, 4B, and 4C, the 3D cursor may be may be implemented in a wide variety of different shapes. Examples include but are not limited to cube, cuboid, cylinder, sphere, ellipsoid, cone and tetrahedron. The shapes are not necessarily regular, and the lengths of edges may be resized, e.g. overall geometric shape scaling or changing individual edges, sides, or surfaces. For example, FIGS. 4A and 4B illustrate cuboid 3D cursors 400, 402 for which edge length has been set or selected based on the dimensions and orientation of the respective feature of interest 404, 406. FIG. 4C illustrates a spherical 3D cursor 408 for which the diameter may be set or selected based on the dimensions of the feature of interest 410. In addition to dimensional changes, cursor geometric shape may be changed.

The ability to change the size, shape, and individual dimensions of the 3D cursor enables the cursor to be customized based on the particular volume of interest to the medical professional. A fixed-shape, fixed-size cursor might be too large or too small, e.g. so as to include a significant amount of tissue not of interest. For example, in examining the lungs, placement of a cube-shaped cursor could cause ribs to be included in the image. Changing the shape of the 3D cursor would help to overcome this limitation. Customization could be accomplished by wide variety of techniques, possibly including but not limited to selecting an edge, side or vertex of the original 3D cursor with a second type of cursor 412, and then "clicking and dragging" the selected edge, side, or vertex in the desired direction to expand or reduce the volume of the original 3D cursor. The interface may also enable selection and change between multiple 3D geometric shapes, e.g. changing from cuboid to spherical. Scrolling on the conventional slices while simultaneously drawing shapes can also be performed to generate the prescribed 3D cursor volume. The interactive 3D cursor thus provides an efficient interface for tissue subtraction to provide enhanced visualization of the tumor.

Figure 5:
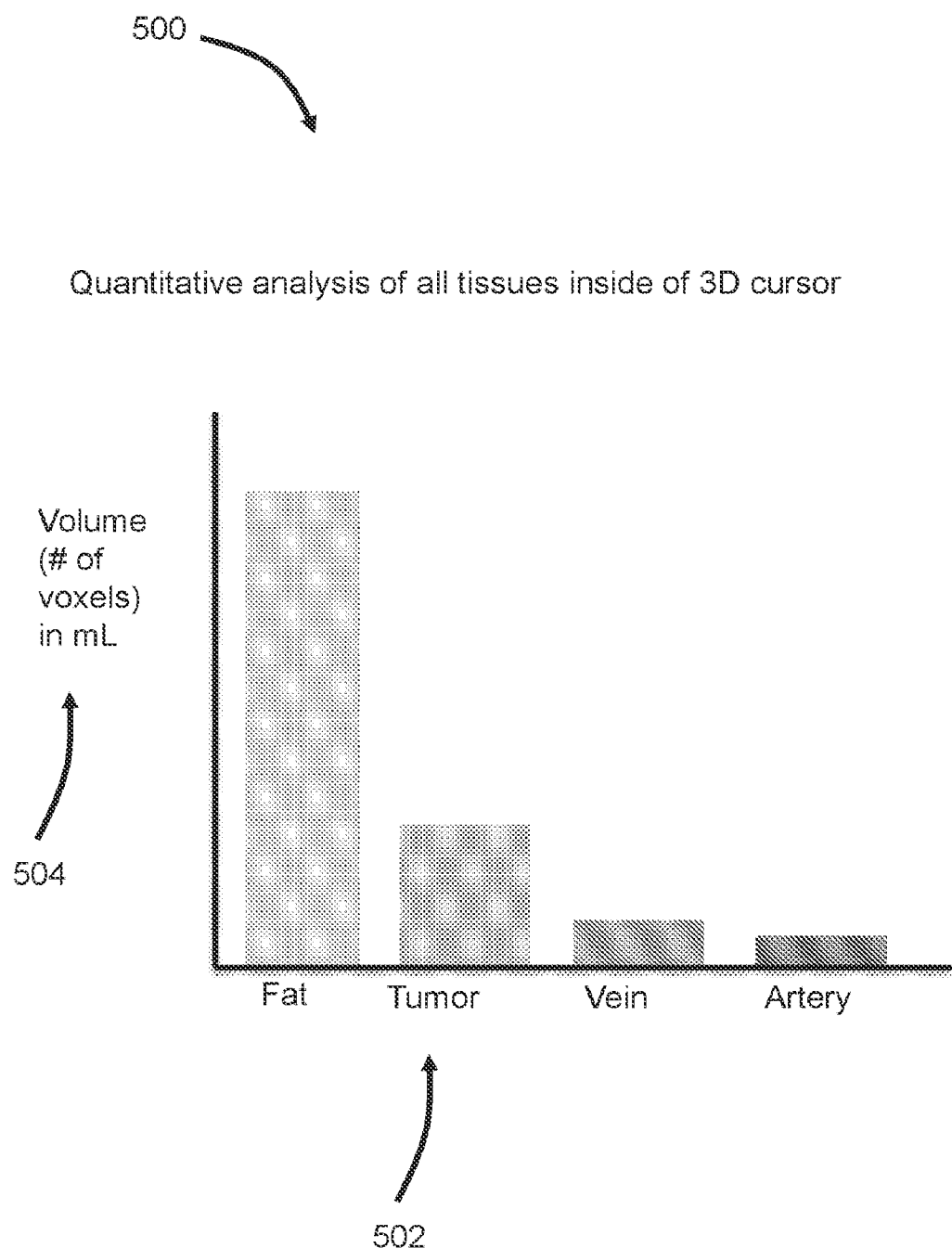
FIG. 5 illustrates presentation of a quantitative analysis of tissues inside of the volume of interest selected with the 3D cursor of FIG. 1A.

FIG. 5 illustrates presentation of a quantitative analysis 500 of all tissues inside a volume selected with the 3D cursor. The illustrated example includes a bar graph but it is to be understood that any of a wide variety of charts, graphs, and other techniques for presentation of data might be implemented. Quantitative analysis can help the radiologist understand how a feature of interest such as tumor 502 (e.g., the lobulated mass 106, FIG. 1B) is changing in volume 504 over multiple time points. The interface may include a statistical representation of the tissue types, possibly including but not limited to a histogram bar chart to depict the volume (e.g., number of voxels per unit volume) of the different types of tissue within the cursor, distinct markings for different types of tissue such as, but not limited to, color coding the bars of the histogram bar chart.

Figure 6:
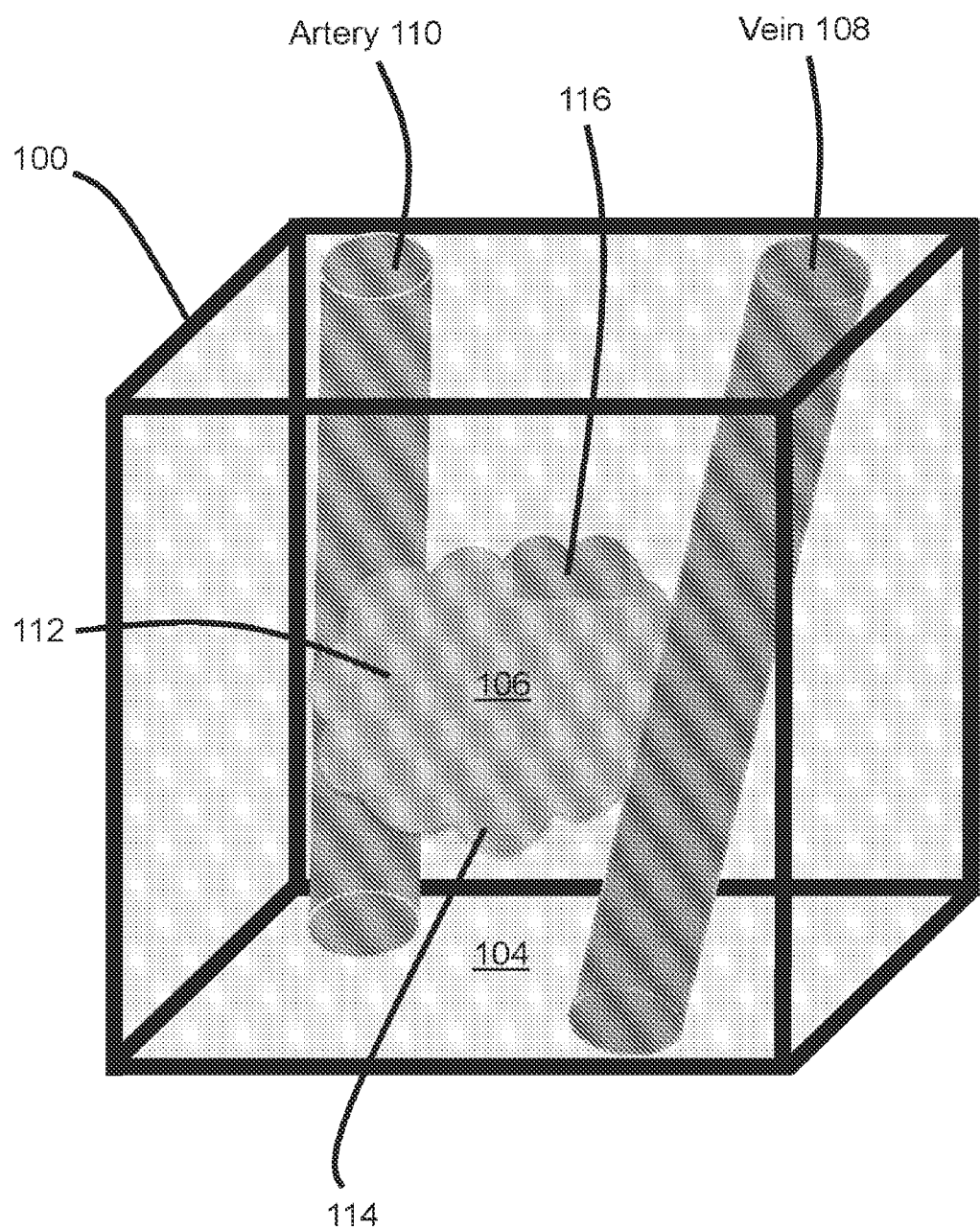
FIG. 6 illustrates use of false color and transparency changes to enhance viewing of the selected volume of interest.

FIG. 6 illustrates an implementation of the interactive 3D cursor 100 with false color and transparency to enhance viewing. False color and transparency may be dynamically adjusted and turned ON and OFF. Different false colors may be applied to different tissue types within the volume of the 3D cursor. The colors could be selected to correspond to the colors used in the statistical representation (FIG. 5). Alternatively, a respective unique false color could be selected for each different tissue type, or tissue types of particular interest or concern, and/or additional features of concern, e.g., irregular margin, indistinct margin, spiculation, etc. In the illustrated example, the background material 104 (fat) is depicted in light gray, the artery 110 is depicted in red, the vein 108 is depicted in blue, and the lobulated mass 106 is multicolored. Different colors may be selected or used to indicate stability of the lobulated mass 106 over time. For example, green may be used to indicate a stable volume 112 while orange is used to denote a slow growth volume 114, thereby providing a visual warning indicator. Red may be used to indicate high rate of growth or concerning margin volume 116. The extent of the volume of the lobulated mass can be determined automatically, e.g. based on density. Moreover, changes in volume of sub-regions of the lobulated mass may also be automatically determined, and color coding may be automatically implemented. This can help the radiologist understand how the mass is changing in volume over multiple time points.

Figure 7:
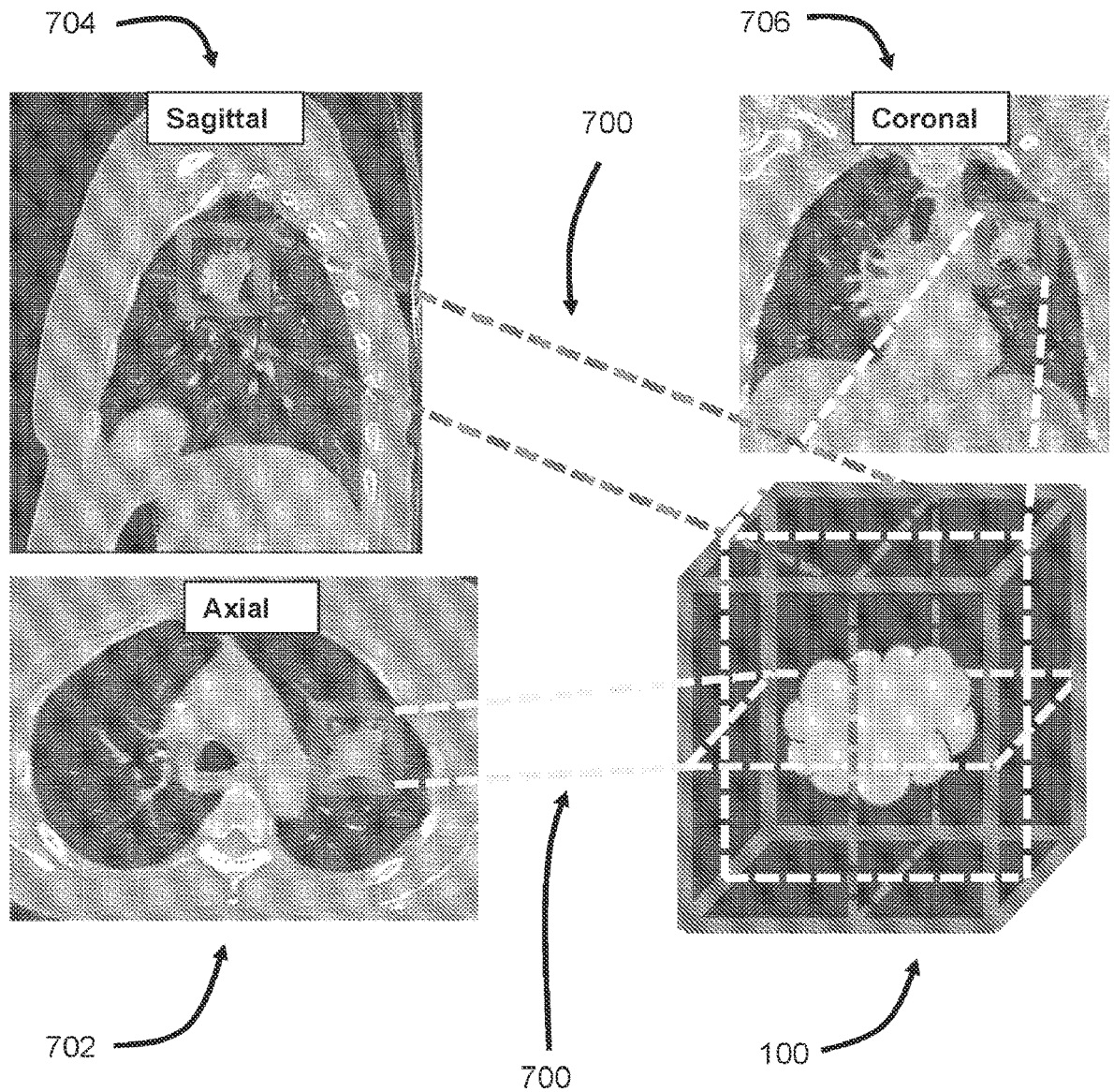
FIG. 7 illustrates association of multiple computed tomography (CT) images of the chest in lung windows with the interactive 3D cursor using reference lines.

FIG. 7 illustrates association of multiple computed tomography (CT) images of the chest in lung windows with the interactive 3D cursor 100 using reference lines 700. The illustrated example includes an axial image 702, a sagittal image 704, and a coronal image 706 of the chest in lung windows. An advantage is enhanced ability to cross reference the 3D cursor to the original 2D slices 702, 704, 706 from which total 3D volume was obtained. Medical professionals have experience and familiarity with 2D slices and may feel more confident in their findings given the capability to switch back and forth between the 2D and 3D volumetric approaches. A small display adjacent to the interactive 3D cursor could indicate which 2D slices contain tissue within in the interactive 3D cursor. Then the medical professional could direct the system to automatically select those slices which have tissue within the cursor and display them on a nearby 2D display unit. A corresponding visible boundary of the 3D cursor (e.g., red) projected on each of the slices may be presented.

Figure 8:
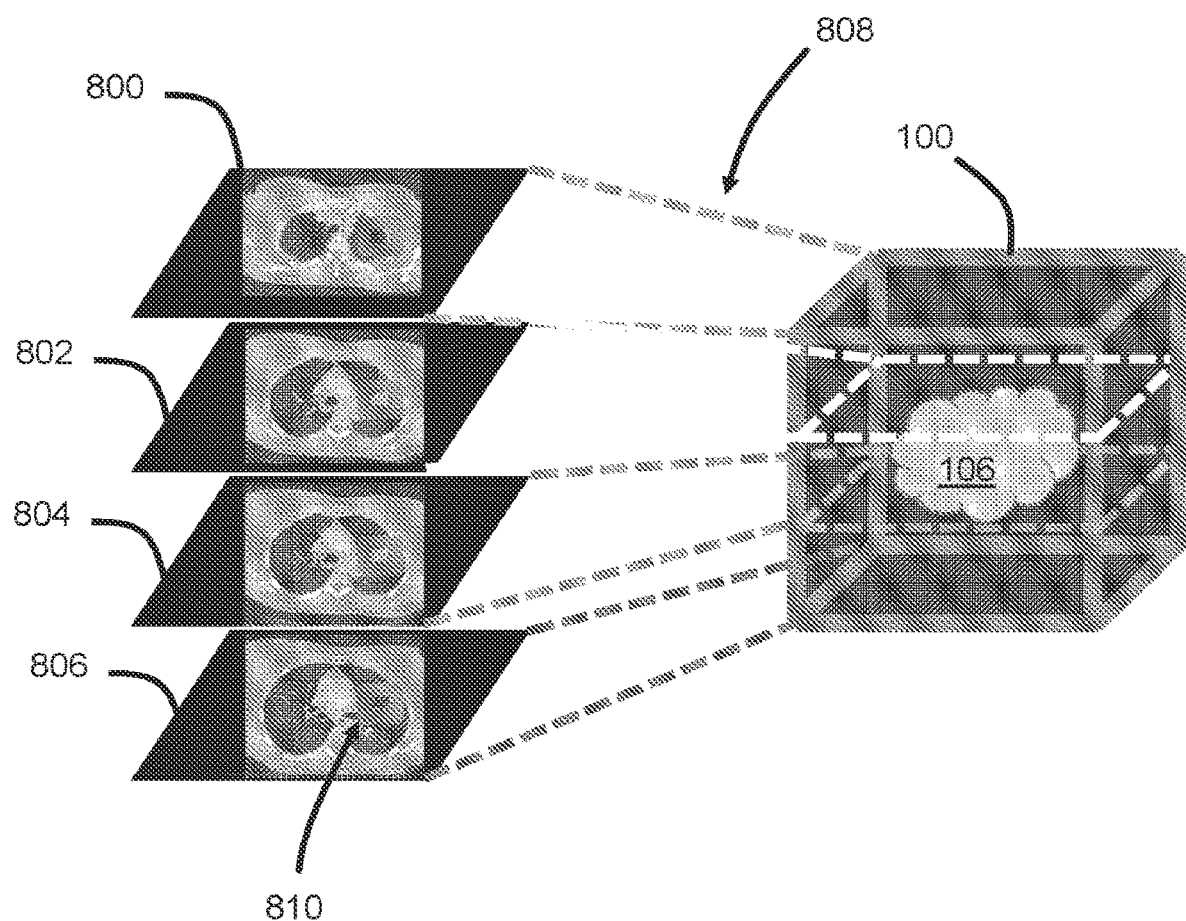
FIG. 8 illustrates association of multiple axial computed tomography (CT) slices of the chest in lung windows with the interactive 3D cursor using reference lines.

FIG. 8 illustrates association of multiple axial computed tomography (CT) slices 800, 802, 804, 806 of the chest in lung windows with the interactive 3D cursor 100 using reference lines 808. The multiple axial computed tomography (CT) slices of the chest in lung windows show the location of the 3D cursor, i.e. the slice area that includes a cross-section of the 3D cursor, which in the illustrated example has selected a left upper lobe mass. Boundaries 810 of the 3D cursor in the slices are depicted in a color, e.g. red. Within the 3D cursor the lung cancer mass 106 is depicted in gray, surrounded by black that indicates non-cancerous lung tissue. This implementation helps the medical professional to rapidly visualize where the interactive 3D cursor is located relative to the slice images and the body. It also enables the medical professional to visualize the entire volumetric data with the interactive 3D cursor accurately positioned within the volume. Transparency of tissue within the 3D volume could be changed so that the interactive 3D cursor would stand out. This would help avoid left-right orientation mistakes that might occur during treatment. Multiple interactive 3D cursors which could be of differing sizes and/or shapes could be created and displayed.

Figure 9:
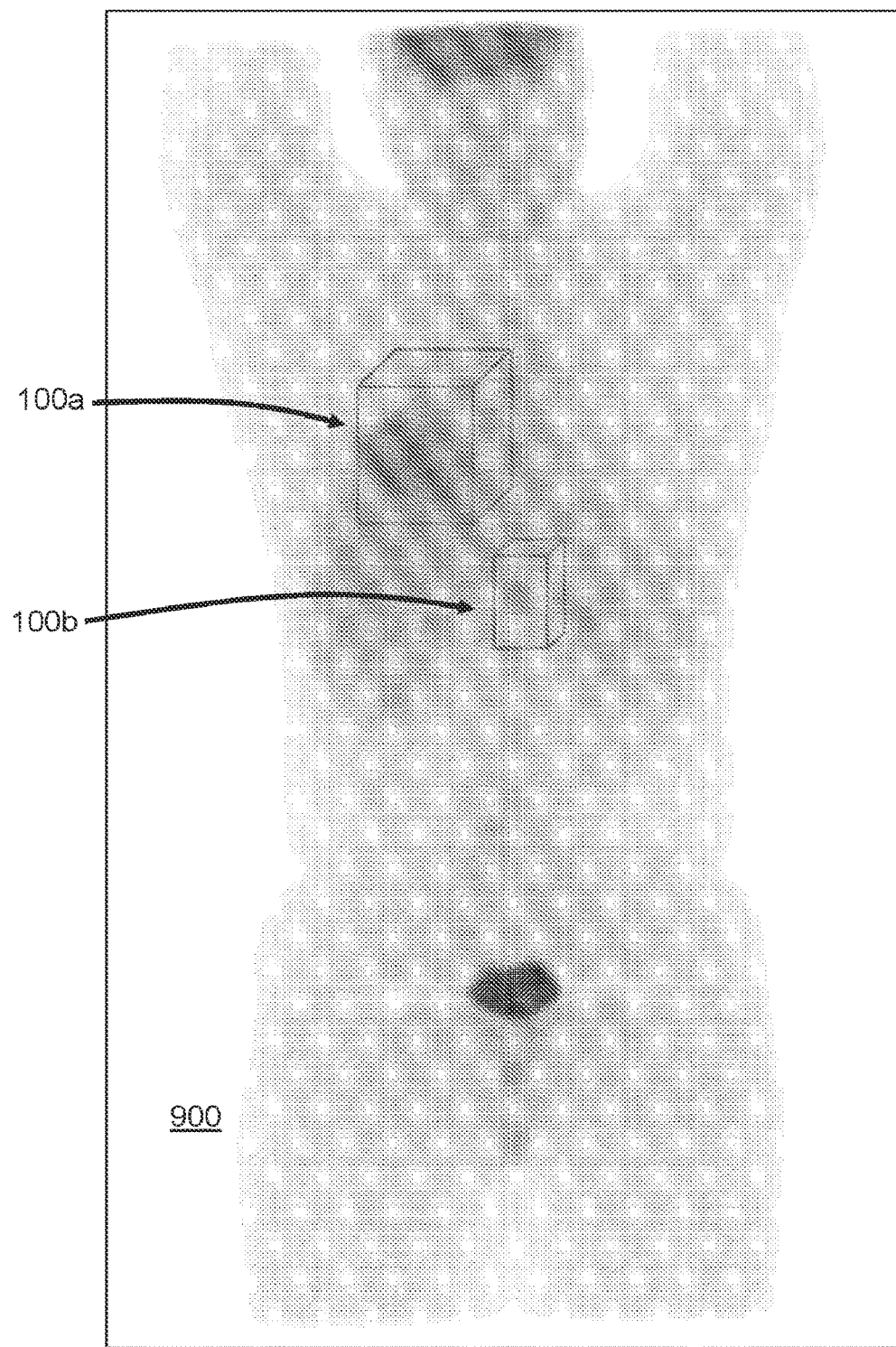
FIG. 9 illustrates a maximum intensity projection (MIP) image of a fludeoxyglucose (18F) positron emission tomography (PET) scan in which two varying sized interactive 3D cursors are overlaid to indicate 3D cursor shape, size, orientation, and location when respective volumes of interest were selected.

FIG. 9 illustrates overlay of 3D cursors 100a, 100b on a maximum intensity projection (MIP) image 900 of a fludeoxyglucose (18F) positron emission tomography (PET) scan. Two different-sized interactive 3D cursors are used to highlight two separate areas of concern, including 3D cursor 100a for a right lung mass and cursor 100b for a vertebral body metastasis. This helps to automatically transfer data (e.g., picture of tissue within the cursor and statistical representations) from the viewing modality to the report of findings. Selection of key data through human machine interface such as, but limited to, a screen capture can be automatically transferred to the report of findings. This would provide quantitative results within the report together with qualitative impressions of the medical professional.

Figure 10:
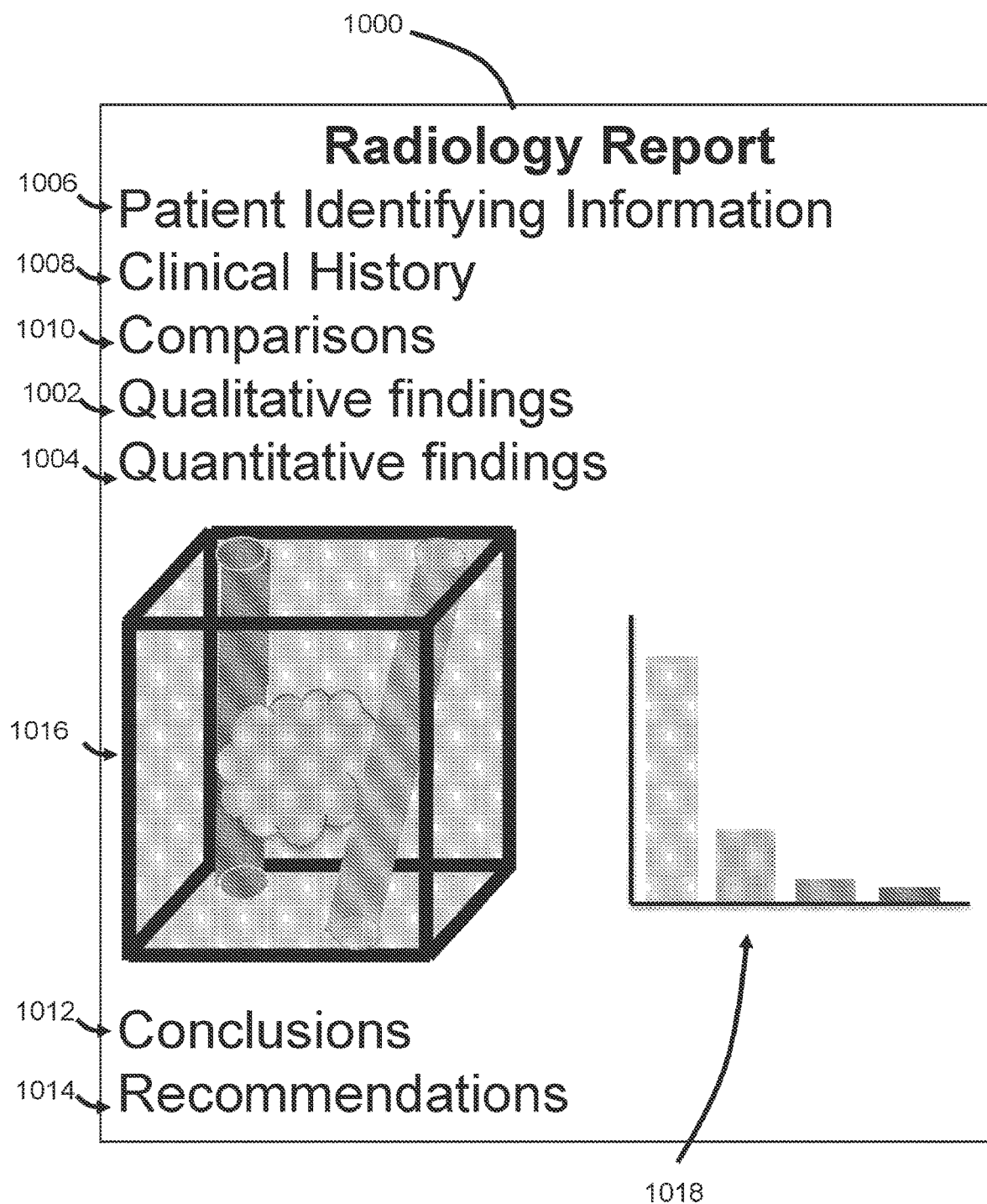
FIG. 10 illustrates a radiology report enhanced with information obtained using the interactive 3D cursor and including quantitative and qualitative analysis.

FIG. 10 illustrates a radiology report 1000 enhanced with information obtained from the interactive 3D cursor. Qualitative findings 1002 and quantitative findings 1004 may be included along with patient identifying information 1006, clinical history 1008, comparisons 1010, conclusions 1012, and recommendations 1014. Also included are a selected volume image 1016 and statistical graphic 1018. This helps to quantitatively track changes in volumes of concern (e.g., tumors) over time.

Figure 11:
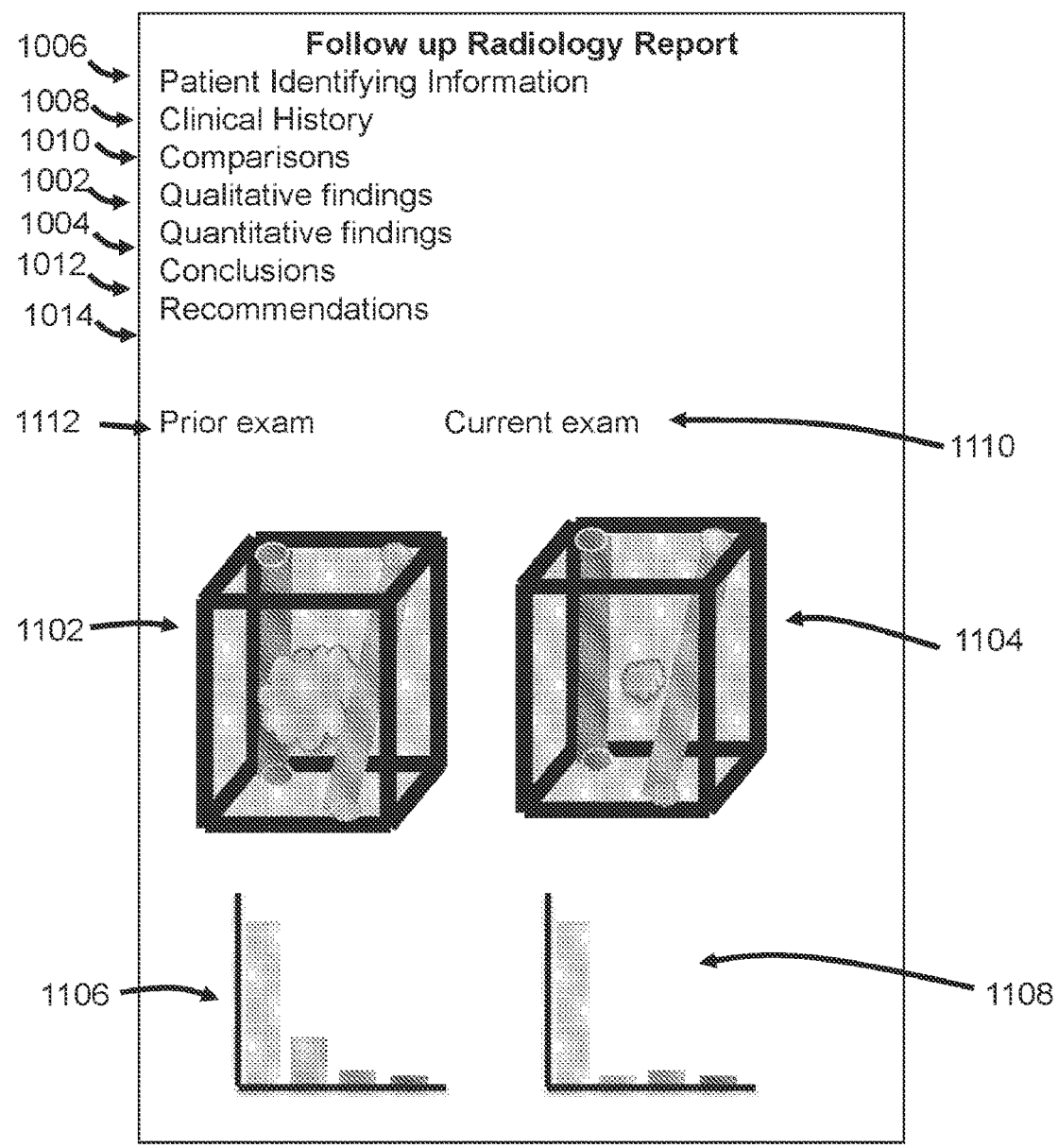
FIG. 11 illustrates a radiology report enhanced with information obtained using the interactive 3D cursor, and including added quantitative and qualitative analysis at multiple time points.

FIG. 11 illustrates a radiology report 1100 enhanced with information obtained from the interactive 3D cursor at multiple time points. Qualitative findings 1002 and quantitative findings 1004 may be included along with patient identifying information 1006, clinical history 1008, comparisons 1010, conclusions 1012, and recommendations 1014. Also included are selected volume images 1102, 1104 from different time points and respective statistical graphics 1106, 1108 from those time points. Follow up reports can include current and prior exams 1110, 1112 with quantitative analysis and qualitative analysis on how the lesion has changed over time. This may facilitate selection of a lesion (e.g., tumor) at multiple time points using an interactive 3D cursor, qualitative assessment of the lesion at multiple time points; and, quantitative assessment of the lesion at multiple time points. This would enable the medical professional to better assess how a particular lesion is changing over time. A report of current findings as outlined in the previous implementation could be placed in a report together with the data obtained from an earlier examination. This would enable tracking over time the progress of treatment or that of changes in tissues of interest/concern.

Figure 12A:
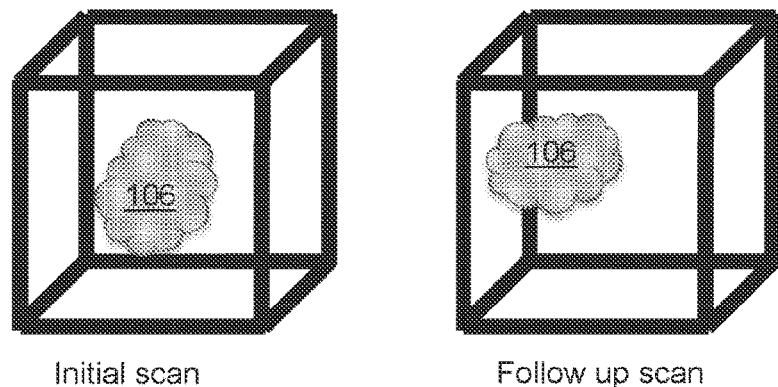
FIGS. 12A, 12B and 12C illustrate a technique for correction for mis-registration at multiple time points using three or more markers.
Figure 12B:
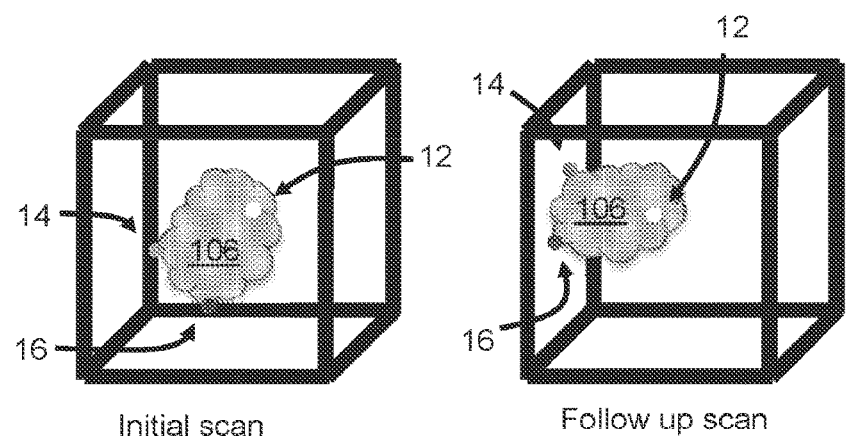
Figure 12C:
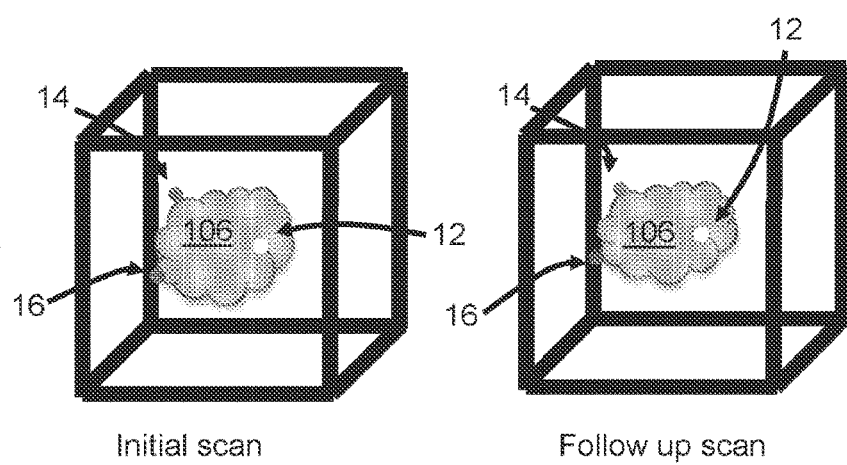

FIGS. 12A, 12B, and 12C illustrate a registration technique by which mis-registration can be corrected at multiple time points through the use of three or more markers 12, 14, 16. Initially, the mass 106 within each 3D cursor 100 image is noted using different locations within the interactive 3D cursor and different orientations. Next, the user marks similar locations on each image of the mass with registration markers. In the illustrated example, a yellow marker 12, a red marker 14, and a blue marker 16 correspond to the same respective parts of the mass on each scan. Finally, tissues within the interactive 3D cursor are aligned in accordance with markers. Many soft tissues within the body can change in orientation from one scan to the next due to patient movement. Corresponding mis-registration can limit the ability to properly track how a lesion changes over time. This technique provides a method to correct for such mis-registration. Three or more recognizable spots of the lesion (e.g., tumor) can be marked with a false color, arrow, or other registration mark. Then, these locations can be automatically aligned with one another. Shadows can be added to help bring out depth perception. Proper alignment will accurately align the shadows. This enhances visual assessment for how a lesion is changing over time to include changes in tumor composition, size and morphology.

Figure 13:
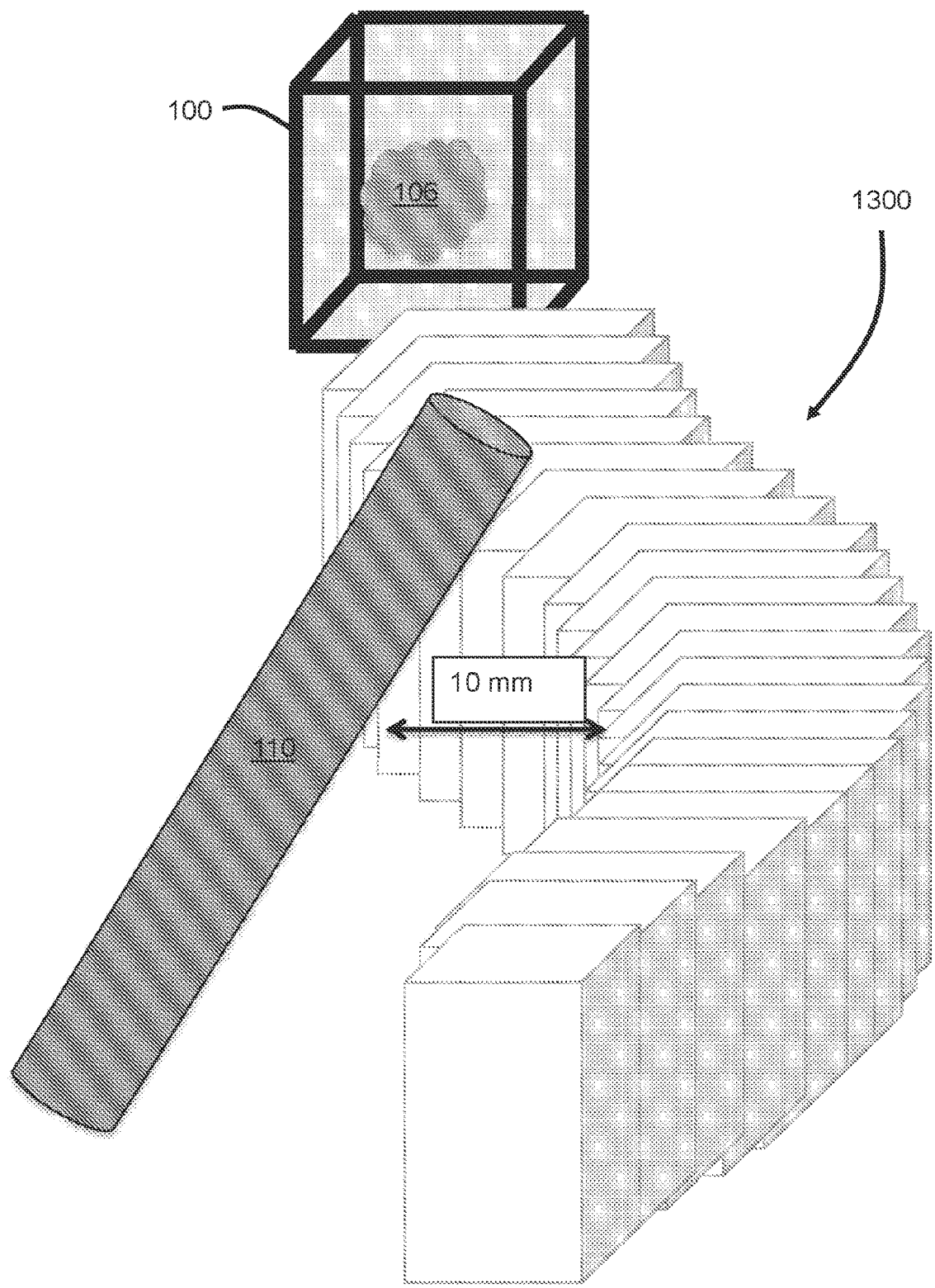
FIG. 13 illustrates use of multiple interactive 3D cursors to select volumes of interest to designate a safe pre-operative planning pathway for guiding surgical intervention.

FIG. 13 illustrates use of multiple image volumes selected with the 3D cursor to designate a safe pre-operative planning pathway to guide surgical intervention. In the illustrated example, multiple green interactive 3D cursors 1300 mark a surgeon-selected dissection pathway that is deemed safe in the pre-operative setting. The interactive 3D cursor 100 containing the cancerous lesion 106 is shown at a distal end of the planned surgical path represented by abutting or overlapping volumes selected with the 3D cursors 1300. The selected path that the surgeon will excise avoids the artery 110 with a minimum clearance of 10 mm. This provides the advantage of 3D depiction of possible surgical cuts. The path could include, but is not limited to, one or more of the following properties: a serpentine shape; measurements could subsequently be made to measure absolute distance between a point on the planned path to some region of concern (e.g., artery); the path could also be projected on a head mounted display at different intervals during the course of the operation. This feature would facilitate surgical planning as well as a potential to improve accuracy of the surgery.

Figure 14:
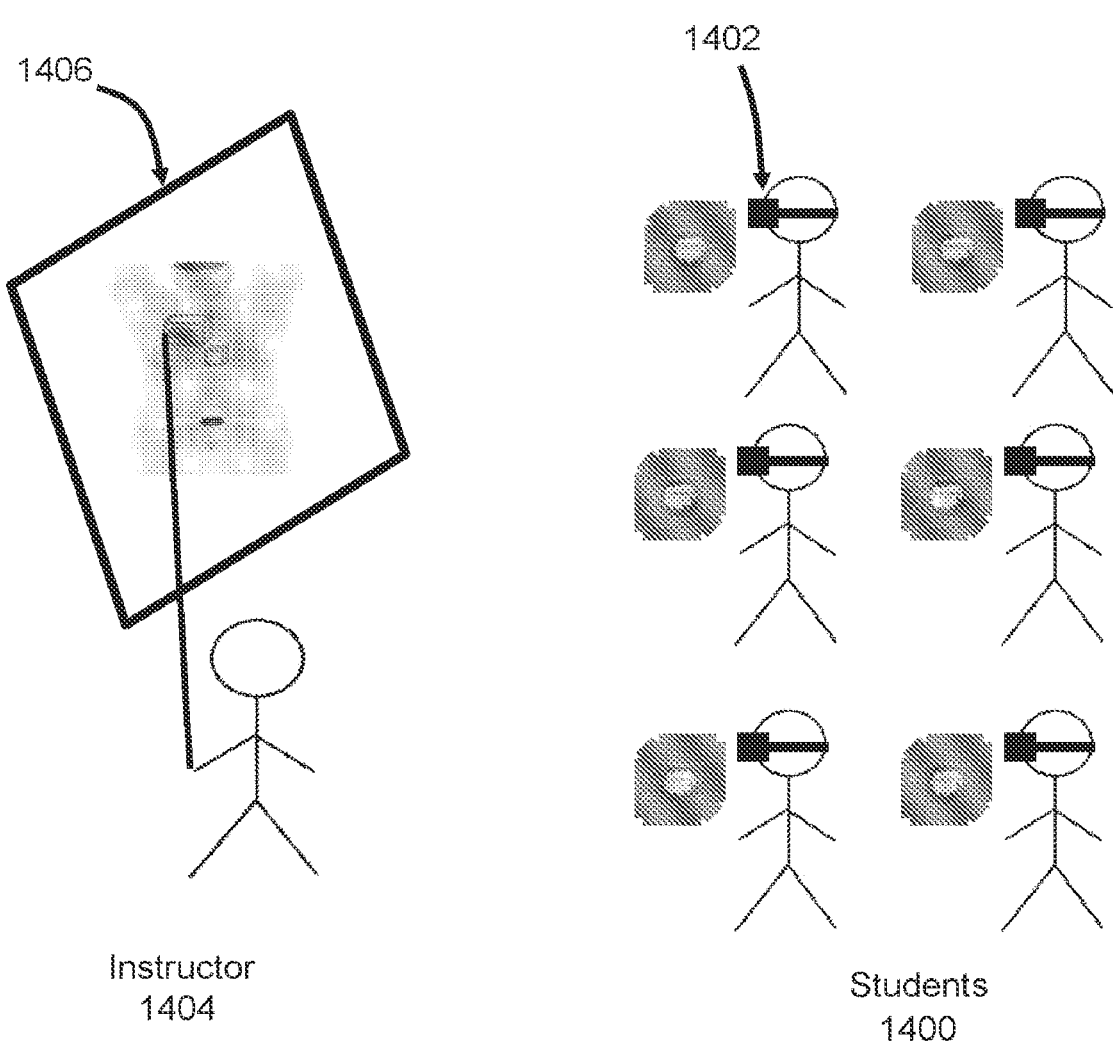
FIG. 14 illustrates use of the interactive 3D cursor in an educational setting.

FIG. 14 illustrates use of the interactive 3D cursor in an educational setting. Students 1400 are depicted wearing AR (augmented reality) headsets 1402 and an instructor 1404 is pointing to an abnormality on the board 1406. This facilitates presentation of medical information (e.g., anatomy) in a classroom environment. The interactive 3D cursor could be placed around the organ of interest and other parts of the body could be eliminated. Items from implementations discussed above such as metrics and arrows could be used. The students would be provided 3D head displays and joined into a display system so that they could see the tissue within the interactive 3D cursor. This would eliminate any confusion on the part of the students as to what specific detail in the imagery was being discussed.

Figure 15:
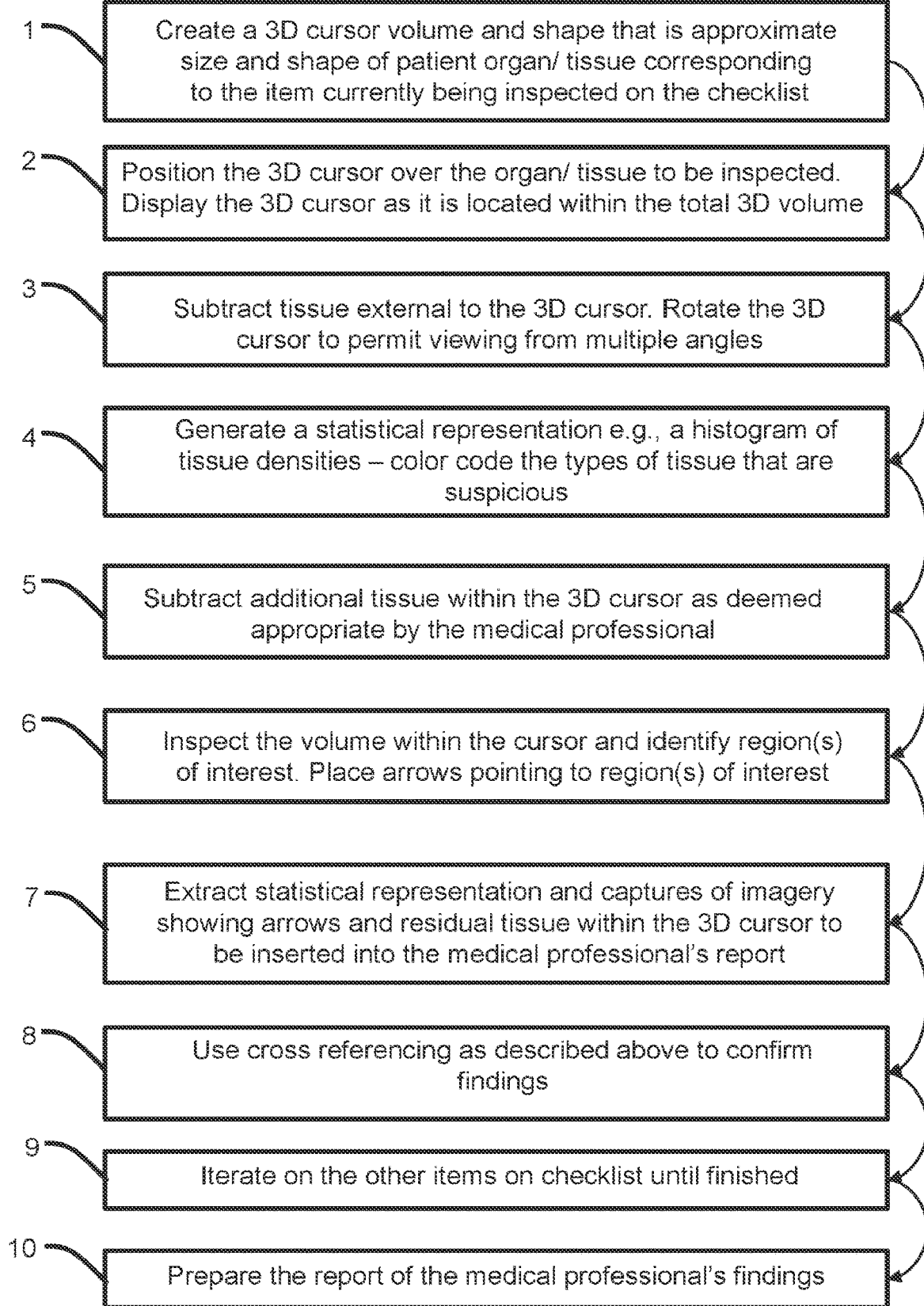
FIG. 15 illustrates process steps on a radiologist's review of a patient's image with integration of the interactive 3D cursor.

FIG. 15 illustrates process steps on a radiologist's review of a patient's image with integration of the interactive 3D cursor into his/her practice. Step 1 is to create an interactive 3D cursor volume and shape that approximates the size and shape of patient organ/tissue corresponding to the item currently being inspected on the checklist. Step 2 is to position the interactive 3D cursor over the organ/tissue to be inspected. The interactive 3D cursor as it is located within the total 3D image volume may be presented on a display. Step 3 is to subtract from view all tissue external to the interactive 3D cursor. The interactive 3D cursor may be rotated to permit viewing from multiple angles. If interactive cursors are used at multiple time points to track how a particular lesion (e.g., tumor) changes over time, the 3D cursors can be rotated in synchrony with on another. Step 4 is to generate a statistical representation e.g., a histogram of tissue densities-color coded with the types of tissue that are suspicious. Step 5 is to subtract from view additional tissue within the interactive 3D cursor as deemed appropriate by the medical professional. Step 6 is to inspect the volume within the cursor and identify region(s) of interest and place indicators, annotations, and registration markers relative to region(s) of interest. Step 7 is to extract a statistical representation and capture imagery showing indicators, annotations, and registration markers and residual tissue within the interactive 3D cursor to be inserted into the medical professional's report. Step 8 is to use cross-referencing as described the above to confirm findings. Step 9 is to iterate on the other items on the checklist until finished. Step 10 is to prepare the report of the medical professional's findings. This procedure provides an opportunity to enhance medical image review process by medical professionals.

Figure 16:
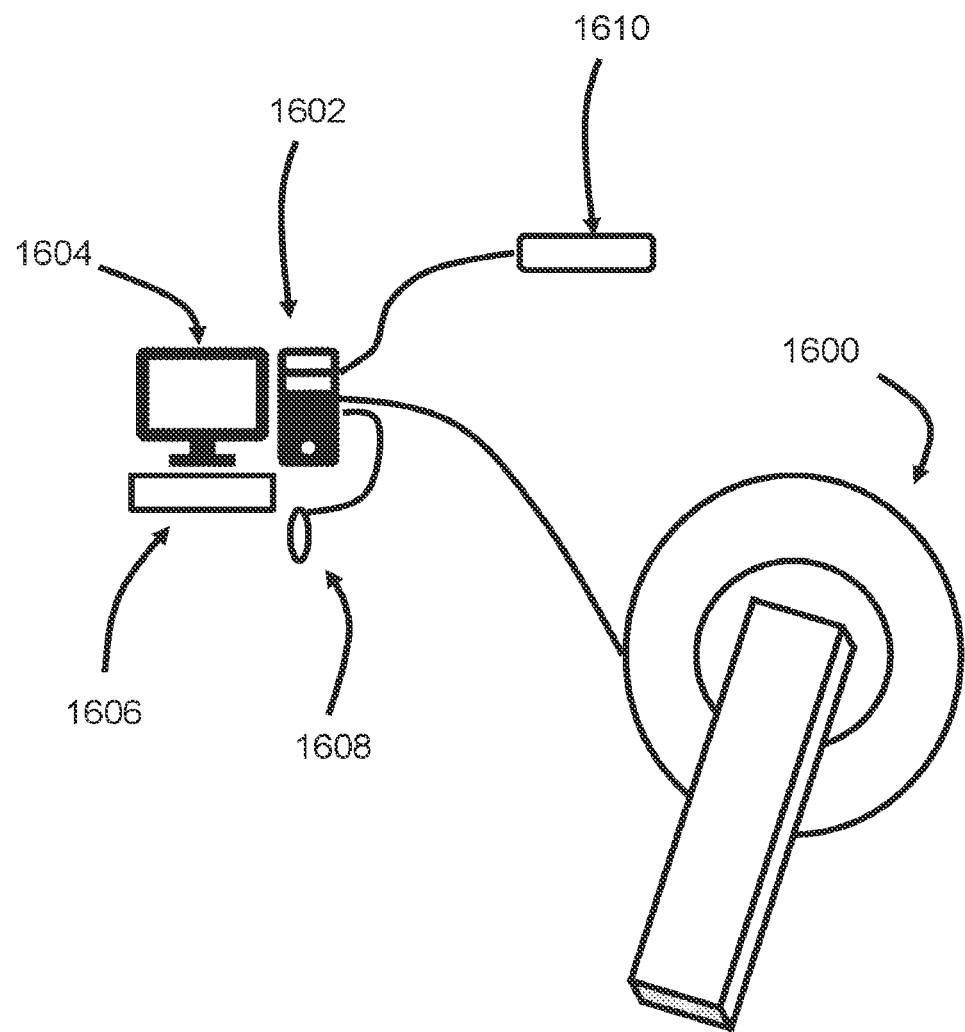
FIG. 16 illustrates a system for use of the interactive 3D cursor.

FIG. 16 illustrates a system for use of the interactive 3D cursor. A medical imaging device 1600 is connected to a computer workstation 1602. A wide variety of medical imaging devices and computer workstations could be used. Images are captured by the medical imaging device and sent to the computer workstation. The computer workstation includes non-volatile storage, computer-readable memory, processors, and a variety of other resources including but not limited to 10 devices that provide a human-machine interface. In the illustrated example, the IO devices include a monitor 1604, keyboard 1606, 3D mouse 1608, and VR headset 1610. The 10 devices are used to prompt a software program that runs on the computer workstation to perform the various process steps and implement the various features that have already been described above.

There are multiple potential advantages of the interactive 3D cursor. For example, there is reduction in time spent for classification of multiple lesions. The radiologist doesn't have to sort through many prior imaging studies to find the lesion and the interactive 3D cursor will save time. There is reduction in error when tracking multiple lesions, i.e. reducing the likelihood of mistakes when identifying different specific lesions that are nearby one another when comparing multiple scans. One possibility is to analyze the images obtained using the 3D cursor and using multiple uniquely tagged (e.g. numbered) cursors for any suspicious regions. The medical profession could then switch to slices for confirmation.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method for displaying a structure in a head display unit, the method comprising:
    obtaining image data representing the structure in a three-dimensional (3D) image space;
    obtaining an initial representation of a 3D cursor in the 3D image space, the 3D cursor having a 3D shape with an initial position in the 3D image space, and the 3D cursor containing the structure;
    obtaining an initial viewing angle for orienting the 3D cursor and the structure in the 3D image space;
    obtaining an initial left eye viewpoint for a left eye and an initial right eye viewpoint for a right eye for viewing the 3D cursor and the structure, wherein the initial right eye viewpoint is offset from the initial left eye viewpoint;
    displaying, by the head display unit, a left eye image for the left eye based on the initial left eye viewpoint, the initial viewing angle, the 3D cursor, and the structure, and a right eye image for the right eye based on the initial right eye viewpoint, the initial viewing angle, the 3D cursor, and the structure;
    obtaining an input to apply a rotation of the 3D cursor containing the structure about the 3D cursor's center;
    responsive to the input, generating an updated viewing angle of the 3D cursor and the structure contained within the 3D cursor to reorient the 3D cursor and the structure in the 3D image space based on the rotation; and
    displaying, by the head display unit, an updated left eye image for the left eye based on the initial left eye viewpoint, the updated viewing angle, the 3D cursor, and the structure, and an updated right eye image for the right eye based on the initial right eye viewpoint, the updated viewing angle, the 3D cursor and the structure.

2. The method of claim 1, further comprising:
    receiving an input to zoom in on the structure contained within the 3D cursor;
    responsive to the input, moving the initial left eye viewpoint to an updated left eye viewpoint closer to the structure and moving the initial right eye viewpoint to an updated right eye viewpoint closer to the structure; and
    displaying, by the head display unit, a further updated left eye image for the left eye and a further updated right eye image for the right eye based on the updated left eye viewpoint and the updated right eye viewpoint.

3. The method of claim 1, further comprising:
    receiving an input to move the initial left eye viewpoint and the initial right eye viewpoint to a different angle with respect to the 3D cursor containing the structure to obtain and moved left eye viewpoint and a moved right eye viewpoint; and
    displaying, by the head display unit, a further updated left eye image for the left eye and a further updated right eye image for the right eye based on the moved left eye viewpoint and moved right eye viewpoint.

4. The method of claim 1, further comprising:
    receiving an input to enlarge the 3D cursor to obtain an enlarged 3D cursor;
    updating the structure's size to obtain an enlarged structure contained within the enlarged 3D cursor; and
    displaying, by the head display unit, a further updated left eye image for the left eye and a further updated right eye image for the right eye based on the enlarged 3D cursor and the enlarged structure.

5. The method of claim 1, further comprising:
    receiving an input to move the 3D cursor within 3D image space from the initial position to a moved position; and
    displaying, by the head display unit, a further updated left eye image for the left eye and a further updated right eye image for the right eye based on the moved position of the 3D cursor.

6. The method of claim 1, wherein obtaining the input to apply the rotation comprises receiving a user control from a human machine interface.

7. The method of claim 1, wherein displaying the updated left eye image and the updated right eye image comprises:
   identifying a center point of the 3D cursor;
   obtaining a left eye center viewing angle and a right eye center viewing angle that converge at the center point; and
   generating the updated left eye image based on the left eye center viewing angle and the updated right eye image based on the right eye center viewing angle.

8. The method of claim 1, further comprising:
   tracking motion of the head display unit;
   generating an updated left eye viewpoint and an updated right eye viewpoint based on the motion; and
   displaying, by the head display unit, a further updated left eye image for the left eye based on the updated left eye viewpoint and a further updated right eye image for the right eye based on the updated right eye viewpoint.

9. The method of claim 1, further comprising:
   receiving an input to apply an image processing function to the structure contained within the 3D cursor; and
   displaying, by the head display unit, a further updated left eye image for the left eye and a further updated right eye image for the right eye based on the image processing function.

10. The method of claim 1, wherein obtaining the initial representation of the 3D cursor comprises:
    receiving an input indicative of a color and size of the 3D cursor; and
    generating the initial representation of the 3D cursor based on the color and size.

11. The method of claim 1, wherein displaying the left eye image and the right eye image comprises:
    determining, for the updated left eye image, left eye pixel angles for respective left eye pixels in the updated left eye image;
    identifying respective left eye voxel cones through the structure for each of the left eye pixel angles; and
    generating respective left eye pixel values for the respective left eye pixels in the updated left eye image based on the respective left eye voxel cones;
    determining, for the right eye image, right eye pixel angles for respective right eye pixels in the updated right eye image;
    identifying respective right eye voxel cones through the structure for each of the right eye pixel angles; and
    generating respective right eye pixel values for the respective right eye pixels in the updated right eye image based on the respective right eye voxel cones.

12. A non-transitory computer-readable storage medium storing instructions for displaying a structure in a head display unit, the instructions when executed by a processor causing the processor to perform steps including:
    obtaining image data representing the structure in a three-dimensional (3D) image space;
    obtaining an initial representation of a 3D cursor in the 3D image space, the 3D cursor having a 3D shape with an initial position in the 3D image space, and the 3D cursor containing the structure;
    obtaining an initial viewing angle for orienting the 3D cursor and the structure in the 3D image space;
    obtaining an initial left eye viewpoint for a left eye and an initial right eye viewpoint for a right eye for viewing the 3D cursor and the structure, wherein the initial right eye viewpoint is offset from the initial left eye viewpoint;
    displaying, by the head display unit, a left eye image for the left eye based on the initial left eye viewpoint, the initial viewing angle, the 3D cursor, and the structure, and a right eye image for the right eye based on the initial right eye viewpoint, the initial viewing angle, the 3D cursor, and the structure;
    obtaining an input to apply a rotation of the 3D cursor containing the structure about the 3D cursor's center;
    responsive to the input, generating an updated viewing angle of the 3D cursor and the structure contained within the 3D cursor to reorient the 3D cursor and the structure in the 3D image space based on the rotation; and
    displaying, by the head display unit, an updated left eye image for the left eye based on the initial left eye viewpoint, the updated viewing angle, the 3D cursor, and the structure, and an updated right eye image for the right eye based on the initial right eye viewpoint, the updated viewing angle, the 3D cursor and the structure.

13. The non-transitory computer-readable storage medium of claim 12, wherein the instructions further cause the processor to perform steps including:
    receiving an input to zoom in on the structure contained within the 3D cursor;
    responsive to the input, moving the initial left eye viewpoint to an updated left eye viewpoint closer to the structure and moving the initial right eye viewpoint to an updated right eye viewpoint closer to the structure; and
    displaying, by the head display unit, a further updated left eye image for the left eye and a further updated right eye image for the right eye based on the updated left eye viewpoint and the updated right eye viewpoint.

14. The non-transitory computer-readable storage medium of claim 12, wherein the instructions further cause the processor to perform steps including:
    receiving an input to move the initial left eye viewpoint and the initial right eye viewpoint to a different angle with respect to the 3D cursor containing the structure to obtain and moved left eye viewpoint and a moved right eye viewpoint; and
    displaying, by the head display unit, a further updated left eye image for the left eye and a further updated right eye image for the right eye based on the moved left eye viewpoint and moved right eye viewpoint.

15. The non-transitory computer-readable storage medium of claim 12, wherein the instructions further cause the processor to perform steps including:
    receiving an input to enlarge the 3D cursor to obtain an enlarged 3D cursor;
    updating the structure's size to obtain an enlarged structure contained within the enlarged 3D cursor; and
    displaying, by the head display unit, a further updated left eye image for the left eye and a further updated right eye image for the right eye based on the enlarged 3D cursor and the enlarged structure.

16. The non-transitory computer-readable storage medium of claim 12, wherein the instructions further cause the processor to perform steps including:
    receiving an input to move the 3D cursor within 3D image space from the initial position to a moved position; and displaying, by the head display unit, a further updated left eye image for the left eye and a further updated right eye image for the right eye based on the moved position of the 3D cursor.

17. The non-transitory computer-readable storage medium of claim 12, wherein obtaining the input to apply the rotation comprises receiving a user control from a human machine interface.

18. The non-transitory computer-readable storage medium of claim 12, wherein displaying the updated left eye image and the updated right eye image comprises:
   identifying a center point of the 3D cursor;
   obtaining a left eye center viewing angle and a right eye center viewing angle that converge at the center point; and
   generating the updated left eye image based on the left eye center viewing angle and the updated right eye image based on the right eye center viewing angle.

19. The non-transitory computer-readable storage medium of claim 12, wherein the instructions further cause the processor to perform steps including:
   tracking motion of the head display unit;
   generating an updated left eye viewpoint and an updated right eye viewpoint based on the motion; and
   displaying, by the head display unit, a further updated left eye image for the left eye based on the updated left eye viewpoint and a further updated right eye image for the right eye based on the updated right eye viewpoint.

20. The non-transitory computer-readable storage medium of claim 12, wherein the instructions further cause the processor to perform steps including:
   receiving an input to apply an image processing function to the structure contained within the 3D cursor; and
   displaying, by the head display unit, a further updated left eye image for the left eye and a further updated right eye image for the right eye based on the image processing function.

21. The non-transitory computer-readable storage medium of claim 12, wherein obtaining the initial representation of the 3D cursor comprises:
   receiving an input indicative of a color and size of the 3D cursor; and
   generating the initial representation of the 3D cursor based on the color and size.

22. The non-transitory computer-readable storage medium of claim 12, wherein displaying the left eye image and the right eye image comprises:
   determining, for the updated left eye image, left eye pixel angles for respective left eye pixels in the updated left eye image;
   identifying respective left eye voxel cones through the structure for each of the left eye pixel angles; and
   generating respective left eye pixel values for the respective left eye pixels in the updated left eye image based on the respective left eye voxel cones;
   determining, for the right eye image, right eye pixel angles for respective right eye pixels in the updated right eye image;
   identifying respective right eye voxel cones through the structure for each of the right eye pixel angles; and
   generating respective right eye pixel values for the respective right eye pixels in the updated right eye image based on the respective right eye voxel cones.

23. A computing system, comprising:
a head display unit;
one or more processors; and
a non-transitory computer-readable storage medium storing instructions for displaying a volume of interest in a head display unit, the instructions when executed causing the one or more processors to perform steps comprising:
   obtaining image data representing a structure in a three-dimensional (3D) image space;
   obtaining an initial representation of a 3D cursor in the 3D image space, the 3D cursor having a 3D shape with an initial position in the 3D image space, and the 3D cursor containing the structure;
   obtaining an initial viewing angle for orienting the 3D cursor and the structure in the 3D image space;
   obtaining an initial left eye viewpoint for a left eye and an initial right eye viewpoint for a right eye for viewing the 3D cursor and the structure, wherein the initial right eye viewpoint is offset from the initial left eye viewpoint;
   displaying, by the head display unit, a left eye image for the left eye based on the initial left eye viewpoint, the initial viewing angle, the 3D cursor, and the structure, and a right eye image for the right eye based on the initial right eye viewpoint, the initial viewing angle, the 3D cursor, and the structure;
   obtaining an input to apply a rotation of the 3D cursor containing the structure about the 3D cursor's center;
   responsive to the input, generating an updated viewing angle of the 3D cursor and the structure contained within the 3D cursor to reorient the 3D cursor and the structure in the 3D image space based on the rotation; and
   displaying, by the head display unit, an updated left eye image for the left eye based on the initial left eye viewpoint, the updated viewing angle, the 3D cursor, and the structure, and an updated right eye image for the right eye based on the initial right eye viewpoint, the updated viewing angle, the 3D cursor and the structure.

* * * * *